(12) United States Patent
Ushijima

(10) Patent No.: US 9,848,758 B2
(45) Date of Patent: Dec. 26, 2017

(54) STEREOSCOPIC ENDOSCOPE SYSTEM

(71) Applicant: OLYMPUS CORPORATION, Tokyo (JP)

(72) Inventor: Takanori Ushijima, Tama (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/967,776

(22) Filed: Dec. 14, 2015

(65) Prior Publication Data

US 2016/0095504 A1 Apr. 7, 2016

Related U.S. Application Data

(63) Continuation of application No. PCT/JP2014/074225, filed on Sep. 12, 2014.

(30) Foreign Application Priority Data

Oct. 8, 2013 (JP) .................................. 2013-211349

(51) Int. Cl.
*A61B 1/04* (2006.01)
*A61N 1/06* (2006.01)
(Continued)

(52) U.S. Cl.
CPC ...... *A61B 1/00193* (2013.01); *A61B 1/00009* (2013.01); *A61B 1/00045* (2013.01);
(Continued)

(58) Field of Classification Search
CPC . A61B 1/00193; A61B 1/00009; A61B 1/045; A61B 1/00006; A61B 1/0005;
(Continued)

(56) References Cited

U.S. PATENT DOCUMENTS 5,522,789 A 6/1996 Takahashi
5,860,912 A * 1/1999 Chiba ................ A61B 1/00059
348/45

(Continued)

FOREIGN PATENT DOCUMENTS

EP 2674099 A1 12/2013
JP H06-194580 A 7/1994

(Continued)

OTHER PUBLICATIONS

Extended Supplementary European Search Report dated Oct. 25, 2016 in related European Patent Application No. 14 85 2731.0.

(Continued)

*Primary Examiner* — Alexandra Newton
(74) *Attorney, Agent, or Firm* — Scully, Scott, Murphy & Presser, P.C.

(57) ABSTRACT

A stereoscopic endoscope system includes a stereoscopic endoscope and an identification information combining section. The stereoscopic endoscope is provided with an R image pickup section and an R output section which are provided on a right side of an endoscope body, an L image pickup section and an L output section which are provided on a left side of the endoscope body, and an R memory and an L memory which store correction information for either right or left and identification information. The right and left image pickup sections and the right and left memories are correctly or incorrectly combined and are connected to the right and left output sections. The identification information combining section performs image combination of an image and identification information inputted from the R output section or an image and identification information inputted from the L output section and outputs a combined image.

8 Claims, 22 Drawing Sheets

(51) Int. Cl.
*A61B 1/00* (2006.01)
*H04N 13/00* (2006.01)
*H04N 13/02* (2006.01)
*G02B 23/24* (2006.01)
*H04N 13/04* (2006.01)
*G03B 35/08* (2006.01)
*H04N 7/18* (2006.01)

(52) U.S. Cl.
CPC ............ *A61B 1/04* (2013.01); *G02B 23/2415* (2013.01); *H04N 13/0029* (2013.01); *H04N 13/0044* (2013.01); *H04N 13/0285* (2013.01); *H04N 13/047* (2013.01); *H04N 13/0429* (2013.01); *G03B 35/08* (2013.01); *H04N 7/18* (2013.01)

(58) Field of Classification Search
CPC ..... A61B 1/051; A61B 1/042; A61B 1/00045; A61B 1/00057; A61B 1/00163; A61B 1/04; H04N 13/0239; H04N 2005/2255; H04N 13/0051; H04N 13/005; H04N 13/0296; H04N 13/044; H04N 13/0048; H04N 13/0438; H04N 13/0497; H04N 2013/0081; H04N 2013/0085; H04N 5/2258; H04N 13/0003; H04N 13/0059; H04N 5/2257; G02B 23/2415; G02B 23/2484
See application file for complete search history.

(56) References Cited

U.S. PATENT DOCUMENTS

| | | |
|---|---|---|
| 8,817,077 B2 | 8/2014 | Urasaki et al. |
| 2012/0004508 A1* | 1/2012 | McDowall ......... A61B 1/00186 600/178 |
| 2012/0182292 A1 | 7/2012 | Shimoyama et al. |
| 2014/0228644 A1* | 8/2014 | Ikenaga ............. A61B 1/00193 600/166 |

FOREIGN PATENT DOCUMENTS

| | | |
|---|---|---|
| JP | H09-160143 A1 | 6/1997 |
| JP | H10-126814 A | 5/1998 |
| JP | 2004-222937 A | 8/2004 |
| JP | 2005-223495 A | 8/2005 |
| WO | WO 2013/031512 A1 | 3/2013 |

OTHER PUBLICATIONS

International Search Report dated Nov. 25, 2014 issued in PCT/JP2014/074225.
Japanese Office Action dated Jun. 3, 2015 issued in JP 2015-509226.

* cited by examiner

FIG. 11

| CASE | OUTPUT SECTION | IMAGE | CORRECTION INFORMATION | OK/NG |
|---|---|---|---|---|
| 1 | R OUTPUT SECTION | R IMAGE | R CORRECTION INFORMATION | OK |
| | L OUTPUT SECTION | L IMAGE | L CORRECTION INFORMATION | |
| 2 | R OUTPUT SECTION | R IMAGE | L CORRECTION INFORMATION | NG (REVERSED CORRECTIONS) |
| | L OUTPUT SECTION | L IMAGE | R CORRECTION INFORMATION | |
| 3 | R OUTPUT SECTION | L IMAGE | L CORRECTION INFORMATION | NG (REVERSED IMAGES) |
| | L OUTPUT SECTION | R IMAGE | R CORRECTION INFORMATION | |
| 4 | R OUTPUT SECTION | L IMAGE | R CORRECTION INFORMATION | NG (REVERSED IMAGES AND REVERSED CORRECTIONS) |
| | L OUTPUT SECTION | R IMAGE | L CORRECTION INFORMATION | |

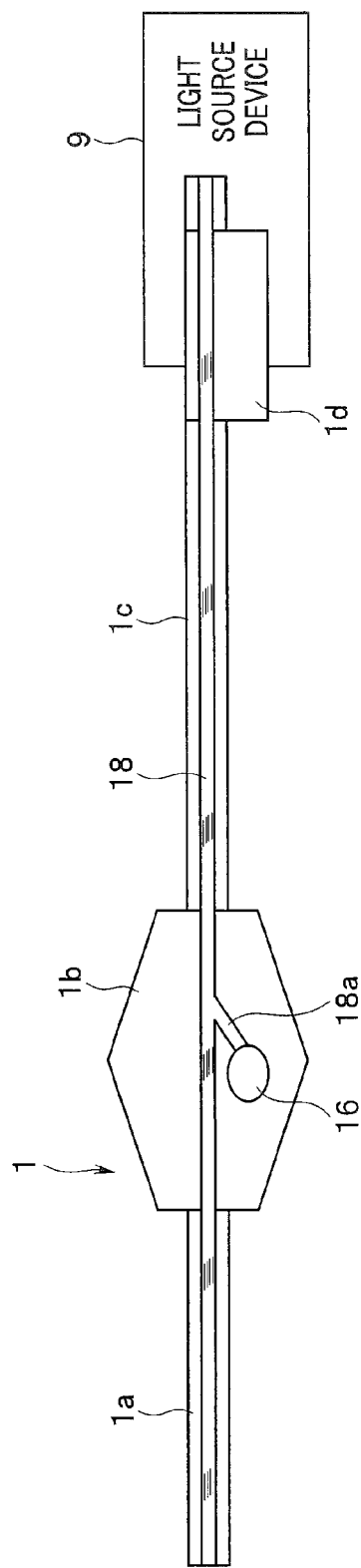
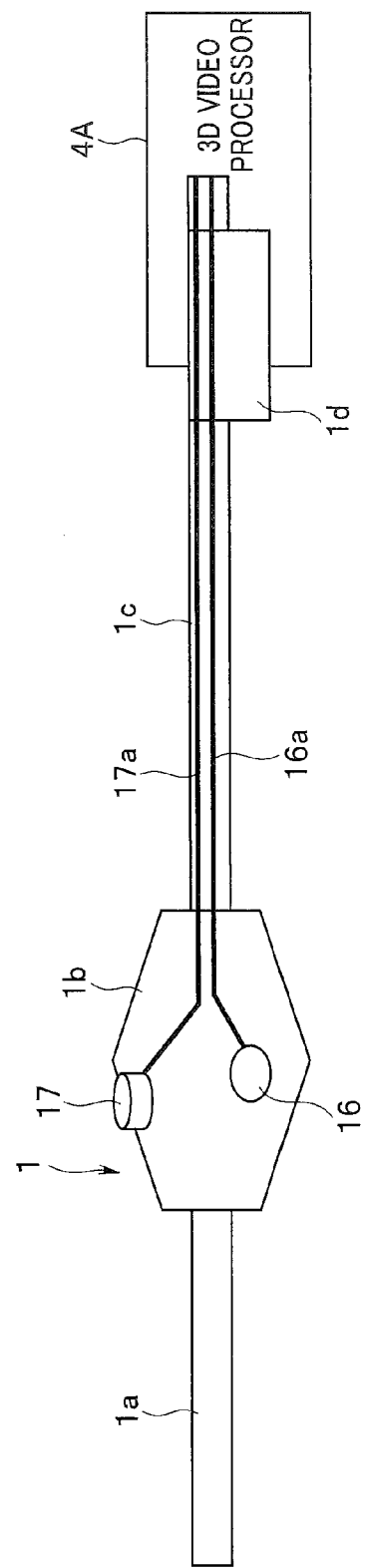

STEREOSCOPIC ENDOSCOPE SYSTEM

CROSS REFERENCE TO RELATED APPLICATION

This application is a continuation application of PCT/JP2014/074225 filed on Sep. 12, 2014 and claims benefit of Japanese Application No. 2013-211349 filed in Japan on Oct. 8, 2013, the entire contents of which are incorporated herein by this reference.

BACKGROUND OF THE INVENTION

1. Field of the Invention

The present invention relates to a stereoscopic endoscope system which includes a stereoscopic endoscope having a right image pickup section and a left image pickup section.

2. Description of the Related Art

A general endoscope apparatus is a so-called 2D endoscope apparatus for observing a subject site as a planar image. However, since the planar image does not give a perspective feeling, a stereoscopic effect cannot be obtained when subtle unevenness or the like on a surface of a body cavity wall is observed as a specific example of the subject site.

Therefore, a stereoscopic endoscope apparatus making it possible to three-dimensionally observe an object has been proposed. A conventional stereoscopic endoscope apparatus is adapted to, for example, form object images with two objective optical systems having a parallax which are provided at a distal end portion, transmit the object images to an eyepiece portion at a rear end portion via a pair of relay optical systems and a pair of eyepiece optical systems, and perform megascopic observation or image pickup by a pair of TV cameras.

As an example of such a conventional stereoscopic endoscope apparatus, for example, a second embodiment of Japanese Patent Application Laid-Open Publication No. 2004-222937 describes a stereoscopic endoscope apparatus which is provided with a right image-forming optical system, a right CCD, an ID memory for outputting a right identification signal, a left image-forming optical system, a left CCD, an ID memory for outputting a left identification signal, and a rearrangement apparatus to which right and left video signals and identification signals are inputted, wherein the rearrangement apparatus outputs a right video signal and a left video signal to odd and even lines of a display device, respectively, based on the identification signals. Here, the display device is such that polarizing plates with polarization directions different from each other by 90 degrees are attached on the odd lines and the even lines, respectively. Therefore, it is possible to three-dimensionally observe an image by observing the display device via a pair of polarizing glasses having a right lens in a polarization direction capable of causing video transmitted through the odd lines to be transmitted and a left lens in a polarization direction capable of causing video transmitted through the even lines to be transmitted. Further, a first embodiment of the official gazette describes a technique in which right video signals and left video signals are sequentially displayed to be stereoscopically observed via a pair of liquid crystal shutter glasses.

Further, Japanese Patent Application Laid-Open Publication No. 10-126814 describes a technique in which a field judging circuit for judging whether each field is for a right eye or for a left eye, and an adding circuit for adding a predetermined display signal to a recording portion in at least one of a judged right eye field and a judged left eye field are provided.

Further, Japanese Patent Application Laid-Open Publication No. 2005-223495 describes a technique in which three-dimensional video displaying means provided with a display surface on which left eye pixels and right eye pixels are alternately arrayed and a parallax barrier which arrays light transmitting areas and light shielding areas alternately according to the array of the right/left eye pixels to generate a parallax, and viewing position confirmation information displaying means for displaying viewing position confirmation information for a left eye and viewing position confirmation information for a right eye within a left half of the display surface and within a right half of the display surface, respectively, are provided so that an observer can determine an appropriate viewing position based on the viewing position confirmation information at time of viewing video.

The technique described in each of the official gazettes described above is a technique utilized at time of using a manufactured stereoscopic endoscope. A point which occurs at time of manufacturing the stereoscopic endoscope will be described with reference to FIGS. 32 to 35.

First, FIG. 32 is a block diagram showing a configuration in which a stereoscopic endoscope in which right and left image pickup sections and right and left memories are reversely connected is observed on a 3D monitor.

A stereoscopic endoscope 101 is provided with: an R image pickup section 112r and an R output section 115r which are arranged on a right side of an endoscope body 111; an L image pickup section 112l and an L output section 115l which are arranged on a left side of the endoscope body 111; an R signal line 113r extended from the R image pickup section 112r; an L signal line 113l extended from the L image pickup section 112l; an R memory 114r which stores R correction information for correcting a right eye image, and an L memory 114l which stores L correction information for correcting a left eye image.

The R image pickup section 112r and the L image pickup section 112l are accurately positioned and assembled so that a right eye image and a left eye image for constituting a stereoscopic image can be acquired, respectively. However, positioning at a pixel pitch level is difficult. Therefore, correction information for cutting out a right eye image acquired from the R image pickup section 112r and a left eye image acquired from the L image pickup section 112l and performing positioning so that a stereoscopic image can be accurately configured is recorded in each of the R memory 114r and the L memory 114l.

A 3D monitor 105 is adapted so that an image outputted from the R output section 115r of the stereoscopic endoscope and an image outputted from the L output section 115l of the stereoscopic endoscope are inputted as a right eye image and a left eye image, respectively, to display a stereoscopic image.

It is assumed that, in such a configuration, the R signal line 113r extended from the R image pickup section 112r is connected to the L memory 114l, and the L signal line 113l extended from the L image pickup section 112l is connected to the R memory 114r due to an assembly mistake.

In this case, a right eye image corrected with L correction information is outputted from the L output section 115l and displayed on the 3D monitor 105 as a left eye image, and a left eye image corrected with R correction information is outputted from the R output section 115r and displayed on the 3D monitor 105 as a right eye image.

Therefore, an inspection using a 2D monitor 103, as shown in FIG. 33, is performed at time of assembly. FIG. 33 is a block diagram showing a configuration in which a manufacturing inspection of the stereoscopic endoscope shown in FIG. 32 is performed with use of a 2D monitor.

The 2D monitor 103 is used by being connected to one of the output sections of the stereoscopic endoscope 101. In the example shown in FIG. 33, the 2D monitor 103 is connected to the L output section 115*l*.

Then, for example, a finger is inserted in an image pickup range of only the L image pickup section 112*l* to confirm whether the finger is displayed on the 2D monitor 103. In an incorrect connection state as shown in FIG. 33, since it is a right eye image picked up by the R image pickup section 112*r* that is outputted from the L output section 115*l*, the finger is not observed on the 2D monitor 103, and it can be detected that the L image pickup section 112*l* is not connected to the L output section 115*l*. Therefore, it is possible to confirm the connection state of the R signal line 113*r* and the L signal line 113*l* again and return the connection state to a correct connection state.

Next, an example in which detection is not possible only by such an inspection method will be described with reference to FIGS. 34 and 35. FIG. 34 is a block diagram showing a configuration in which a stereoscopic endoscope in which pieces of correction information to be stored into memories are stored with left and right reversed is observed on a 3D monitor; and FIG. 35 is a block diagram showing a configuration in which a manufacturing inspection of the stereoscopic endoscope shown in FIG. 34 is performed with use of a 2D monitor.

A right eye image should be corrected with R correction information, and a left eye image should be corrected with L correction information. However, in the example shown in FIGS. 34 and 35, the R correction information and the L correction information are reversely stored in the memories. Therefore, the R image pickup section 112*r* is connected to the L memory 114*l* and the R output section 115*r*, and the L image pickup section 112*l* is connected to the R memory 114*r* and the L output section 115*l*.

At this time, when the 2D monitor 103 is connected to the L output section 115*l*, and a finger is inserted in the image pickup range of only the L image pickup section 112*l*, the finger is displayed on the 2D monitor 103, and the connection state of the image pickup sections appears to be correct at a glance. It is difficult to confirm whether a displayed left eye image has been correctly corrected with L correction information or incorrectly corrected with R correction information, by observing only the 2D monitor 103.

Therefore, it is also conceivable to actually observe and confirm a stereoscopic image further using a 3D monitor, as shown in FIG. 34. It is known, however, that an ability to recognize a stereoscopic image varies among individuals. Some literatures describe that about 10% of people cannot recognize a stereoscopic image as 3D. Therefore, even if a stereoscopic image is displayed with use of a 3D monitor to perform an inspection for confirming whether correction information is correct or incorrect by visual inspection, a correct inspection result cannot be necessarily obtained.

SUMMARY OF THE INVENTION

A stereoscopic endoscope system according to a certain aspect of the present invention is a stereoscopic endoscope system comprising a stereoscopic endoscope, the stereoscopic endoscope system comprising: the stereoscopic endoscope comprising: an endoscope body; a right image pickup section provided on a right side of the endoscope body and acquiring a right eye image; a left image pickup section provided on a left side of the endoscope body and acquiring a left eye image; a right memory associated with one of the right image pickup section and the left image pickup section and storing correction information for right for correcting the right eye image so that the right eye image is for stereoscopy, and right identification information for identifying that what is stored is the correction information for right; a left memory associated with another of the right image pickup section and the left image pickup section and storing correction information for left for correcting the left eye image so that the left eye image is for stereoscopy, and left identification information for identifying that what is stored is the correction information for left; a right output section provided on the right side of the endoscope body and outputting one of a first identification information/image set constituted by the right-eye image and one of the right identification information and the left identification information associated with the right image pickup section and a second identification information/image set constituted by the left eye image and another of the right identification information and the left identification information associated with the left image pickup section at time of a manufacturing inspection; and a left output section provided on the left side of the endoscope body, and outputting another of the first identification information/image set and the second identification information/image set at the time of the manufacturing inspection; and an identification information combining section capable of performing image combination of an image and identification information of an identification information/image set inputted from the right output section to output a combined image as a right output image and performing image combination of an image and identification information of an identification information/image set inputted from the left output section to output a combined image as a left output image.

BRIEF DESCRIPTION OF THE DRAWINGS

FIG. 11 is a diagram showing correct/incorrect classifications of association among the right and left output sections, images and pieces of correction information in the above first embodiment;

FIG. 26 is a diagram showing a configuration example in which a light source of the hand illuminating section is also used as a light source of illuminating light to a distal end portion of the insertion portion of the stereoscopic endoscope in the above first embodiment;

FIG. 27 is a diagram showing a configuration example in which a light emission source is provided on the hand illuminating section to perform control via a 3D video processor in the above first embodiment;

DETAILED DESCRIPTION OF THE PREFERRED EMBODIMENTS

An embodiment of the present invention will be described below with reference to drawings.

First Embodiment

Figure 1:
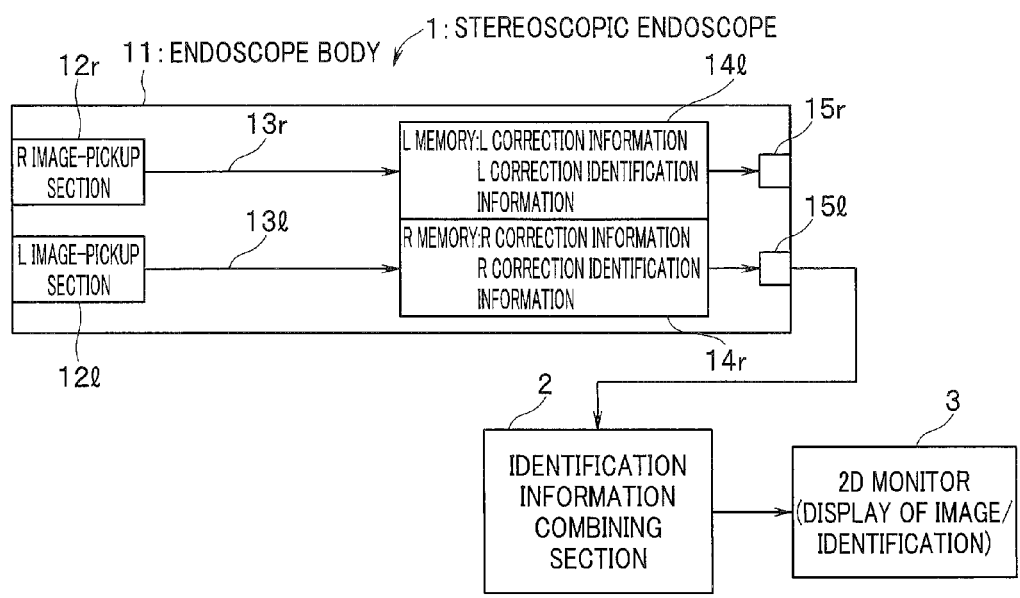
FIG. 1 is a block diagram showing a configuration of a stereoscopic endoscope system in which right and left connections are incorrectly made at time of manufacture in a first embodiment of the present invention.

FIGS. 1 to 31 show a first embodiment of the present invention, and FIG. 1 is a block diagram showing a configuration of a stereoscopic endoscope system in which right and left connections are incorrectly made at time of manufacture.

The stereoscopic endoscope system of the present embodiment is provided with a stereoscopic endoscope 1, an identification information combining section 2 and a 2D monitor 3.

The stereoscopic endoscope 1 has an endoscope body 11, an R image pickup section 12r, which is a right image pickup section, an L image pickup section 12l, which is a left image pickup section, an R signal line 13r, which is a right signal line extended from the R image pickup section 12r, an L signal line 13l, which is a left signal line extended from the L image pickup section 12l, an R memory 14r, which is a right memory, an L memory 14l, which is a left memory, an R output section 15r, which is a right output section, and an L output section 15*l*, which is a left output section. Note that right or a right eye is indicated by R, and left or a left eye is indicated by L below.

The R image pickup section 12*r* is provided on a right side of a distal end of the endoscope body 11 to acquire a right eye image.

The L image pickup section 12*l* is provided on a left side of the distal end of the endoscope body 11 to acquire a left eye image.

Here, when same image pickup sections are used as the right and left image pickup sections, an image pickup section incorporated on a right side of the endoscope body 11 becomes the R image pickup section 12*r*, and an image pickup section incorporated on a left side of the endoscope body 11 becomes the L image pickup section 12*l*. It can be thought that, when different image pickup sections are used as the right and left image pickup sections, they can be identified from incorporated appearances, and it does not happen that the right and left image pickup sections are reversely incorporated relative to the endoscope body 11 (that is, it does not happen that the L image pickup section 12*l* is incorporated on the right side of the endoscope body 11, and it does not happen that the R image pickup section 12*r* is incorporated on the left side of the endoscope body 11).

The R memory 14*r* is associated with one of the R image pickup section 12*r* and the L image pickup section 12*l*, and stores R correction information, which is correction information for right for correcting a right eye image so that the right eye image is for stereoscopy, and R correction identification information, which is right identification information for identifying that what the R memory 14*r* stores is the R correction information. Here, the R correction information is correction information for cutting out a right eye image acquired from the R image pickup section 12*r* and performing positioning so that a stereoscopic image can be accurately configured.

The L memory 14*l* is associated with the other of the R image pickup section 12*r* and the L image pickup section 12*l*, and stores L correction information, which is correction information for left for correcting a left eye image so that the left eye image is for stereoscopy, and L correction identification information, which is left identification information for identifying that what the L memory 14*l* stores is the L correction information. Here, the L correction information is correction information for cutting out a left eye image acquired from the L image pickup section 12*l* and performing positioning so that a stereoscopic image can be accurately configured.

Note that it can be thought that, since the correction information and the identification information are collectively stored in the memory, it does not happen that R/L inconsistency between the correction information and the identification information occurs (that is, it does not happen that R correction information and L correction identification information are stored in the same memory, and it does not happen that L correction information and R correction identification information are stored in the same memory).

Further, though an example in which the R image pickup section 12*r* or the L image pickup section 12*l* is directly connected and associated with the R memory 14*r* or the L memory 14*l* is shown in the present embodiment, they do not have to be directly connected. More generally, an image pickup section (12*r* or 12*l*) which has picked up an image outputted from one of the R output section 15*r* and the L output section 15*l* and a memory (14*r* or 14*l*) which stores correction information outputted from the same one output section are in a relationship of being mutually associated, and, similarly, an image pickup section (12*l* or 12*r*) which has picked up an image outputted from the other of the R output section 15*r* and the L output section 15*l* and a memory (14*l* or 14*r*) which stores correction information outputted from the other output section are in a relationship of being mutually associated.

The R output section 15*r* is provided on the right side of the endoscope body 11, and outputs one of a first identification information/image set constituted by a right eye image and one of the right identification information and the left identification information which is associated with the R image pickup section 12*r* and a second identification information/image set constituted by a left eye image and the other of the right identification information and the left identification information which is associated with the L image pickup section 12*l* at the time of a manufacturing inspection.

The L output section 15*l* is provided on the left side of the endoscope body 11, and outputs the other of the first identification information/image set and the second identification information/image set at the time of the manufacturing inspection.

Here, it can be thought that, since output sections arranged on the right and left sides of the endoscope body 11 become the R output section 15*r* and the L output section 15*l*, respectively, it does not happen that the right and left output sections are reversed (that is, it does not happen that the L output section 15*l* is arranged on the right side of the endoscope body 11, or the R output section 15*r* is arranged on the left side of the endoscope body 11).

Further, the identification information combining section 2 can perform image combination of an image and identification information of an identification information/image set inputted from the R output section 15*r* to output a combined image as a right output image, and can perform image combination of an image and identification information of an identification information/image set inputted from the L output section 15*l* to output a combined image as a left output image.

The 2D monitor 3 is a display device which displays a two-dimensional image. The 2D monitor 3 is connected to the identification information combining section 2 such that at least one of a right output image and a left output image can be inputted, and displays a right output image, a left output image, or right and left output images inputted.

Note that FIG. 1 shows an example in which the R image pickup section 12*r* is connected to the R output section 15*r*, being associated with the L memory 14*l*, and the L image pickup section 12*l* is connected to the L output section 15*l*, being associated with the R memory 14*r* (that is, an example in which correct assembly is not established).

That is, in the example shown in FIG. 1, the R signal line 13*r* extended from the R image pickup section 12*r* is connected to the L memory 14*l* and furthermore connected to the R output section 15*r*. Further, the L signal line 13*l* extended from the L image pickup section 12*l* is connected to the R memory 14*r* and furthermore connected to the L output section 15*l*.

In the example shown in FIG. 1, the identification information combining section 2 and the 2D monitor 3 are connected to the L output section 15*l*.

According to such a configuration, an image and identification information combined with the image are to be displayed on the 2D monitor 3.

Figure 2:
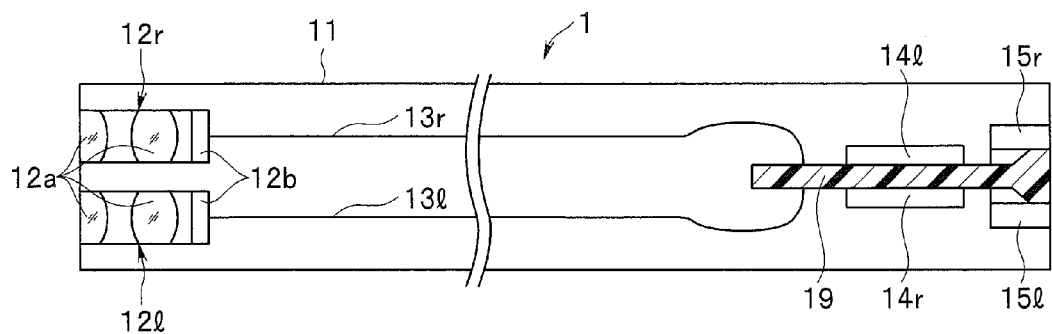
FIG. 2 is a diagram showing a more specific configuration of the stereoscopic endoscope in which the right and left connections are incorrectly made in the above first embodiment.

Next, FIG. 2 is a diagram showing a more specific configuration of the stereoscopic endoscope 1 in which right and left connections are incorrectly made.

The R image pickup section 12r and the L image pickup section 12l are each provided with an objective optical system 12a, and an image pickup device 12b which performs photoelectric conversion of an optical image formed by the objective optical system 12a to output an image.

The R signal line 13r and the L signal line 13l are connected, for example, to one face and the other face on a distal end side of a substrate 19, respectively, and memories are implemented on the one face and the other face of the substrate 19. By L correction information and L correction identification information being stored into the memory implemented on one face of the substrate 19, the memory becomes the L memory 14l. Similarly, by R correction information and R correction identification information being stored in the memory implemented on the other face of the substrate 19, the memory becomes the R memory 14r. Moreover, the R output section 15r and the L output section 15l are implemented on one face and the other face on a proximal end side of the substrate 19, respectively.

Figure 3:
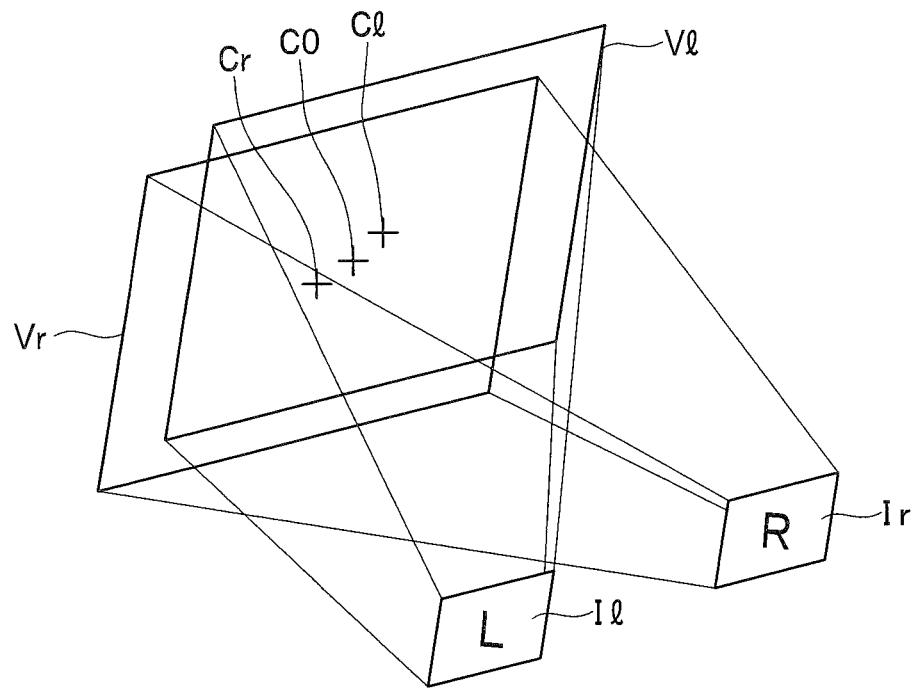
FIG. 3 is a diagram for illustrating R correction information and L correction information in the above first embodiment.

Next, FIG. 3 is a diagram for illustrating the R correction information and the L correction information.

Even if the R image pickup section 12r and the L image pickup section 12l are accurately assembled to the endoscope body 11, it is generally difficult to cause a cross point formed by a center Cr of an observation image Vr at time of observing a right eye image Ir picked up by the R image pickup section 12r by a right eye as it is and a center Cl of an observation image Vl at time of observing a left eye image Il picked up by the L image pickup section 12l by a left eye as it is to completely correspond to a certain particular position at time of assembly.

Correction information for electrically cutting out a right eye image Ir to be displayed, from an image acquired by a right eye, and a left eye image Il to be displayed, from an image acquired by a left eye in order to cause the cross point formed by the center of the observation image Vr and the center of the observation image Vl to correspond to a certain particular fixed point CO after assembly are R correction information and L correction information, respectively.

Figure 4:
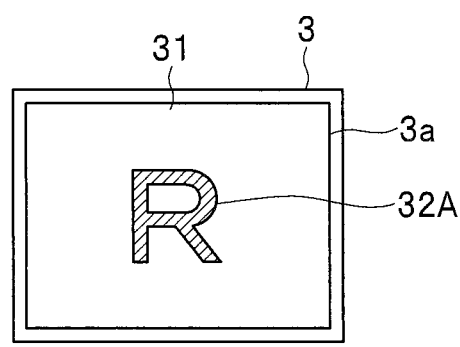
FIG. 4 is a diagram showing a first display example of a 2D monitor at time of a manufacturing inspection in the above first embodiment.
Figure 5:
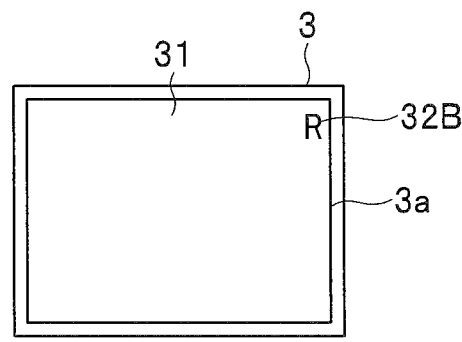
FIG. 5 is a diagram showing a second display example of the 2D monitor at the time of a manufacturing inspection in the above first embodiment.

Some display examples of the 2D monitor 3 will be described with reference to FIGS. 4 to 6. FIG. 4 is a diagram showing a first display example of the 2D monitor 3 at the time of a manufacturing inspection; FIG. 5 is a diagram showing a second display example of the 2D monitor 3 at the time of a manufacturing inspection; and FIG. 6 is a diagram showing a third display example of the 2D monitor 3 at the time of a manufacturing inspection.

In the configuration example shown in FIG. 1, a left eye image picked up by the L image pickup section 12l and R correction identification information stored in the R memory 14r are image-combined by the identification information combining section 2 and displayed on a screen 3a of the 2D monitor 3.

A same image 31 is displayed in FIGS. 4 and 5. As for how to display identification information, however, identification information 32A of the first display example shown in FIG. 4 is a character "R" indicating that correction is performed by R correction information, which is semi-transparently displayed relatively large on a central part of the screen 3a, while identification information 32B of the second display example shown in FIG. 5 is similarly the character "R", which is non-transparently displayed, for example, at an upper-right corner part of the screen 3a in order not to easily obstruct observation of the image 31.

Figure 6:
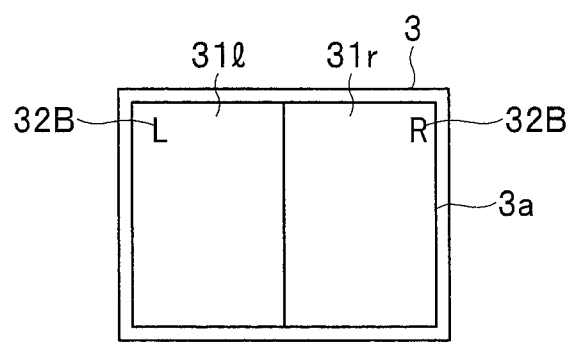
FIG. 6 is a diagram showing a third display example of the 2D monitor at the time of a manufacturing inspection in the above first embodiment.

Further, if the 2D monitor 3 is a monitor of such a type that images of a plurality of systems can be simultaneously inputted and can be dividedly displayed on the screen 3a, it is preferred to output an output from the L output section 15l to the 2D monitor 3 via the identification information combining section 2 and, furthermore, simultaneously output an output from the R output section 15r to the 2D monitor 3 via the identification information combining section 2 to perform display, for example, as shown in FIG. 6.

In the third display example shown in FIG. 6, an output from the R output section 15r is displayed on a right-side half of the screen 3a, and an output from the L output section 15l is displayed on a left-side half of the screen 3a. At this time, for example, in an aspect similar to that of FIG. 5, identification information 32B (here, characters "R") indicating that the image has been outputted from the R output section 15r and identification information 32B (here, characters "L") indicating that the image has been outputted from the L output section 15l are non-transparently displayed on an upper-right corner part on the right-side half of the screen 3a and an upper-left corner part of the left-side half of the screen 3a, respectively.

Note that, in the example shown in FIG. 6, since a right eye image 31r and the character "R", which is the R correction identification information, are displayed on the right-side half of the screen 3a, and a left eye image 31l and the character "L", which is the L correction identification information, are displayed on the left-side half of the screen 3a, the example is an example in which connections of the R and L image pickup sections 12r and 12l, the R and L memories 14r and 14l, and the R and L output sections 15r and 15l in the stereoscopic endoscope 1 are correctly connected.

Figure 7:
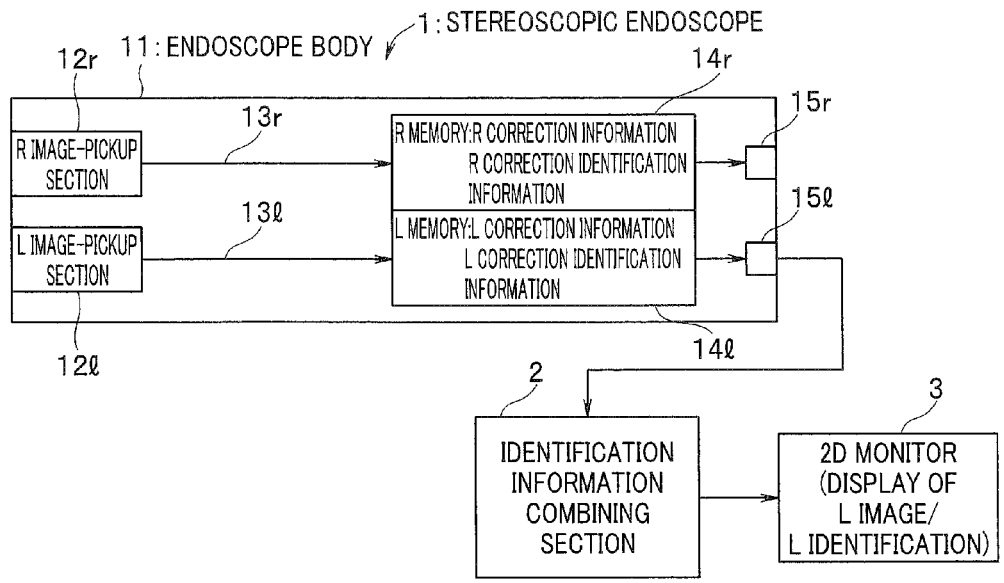
FIG. 7 is a block diagram showing a configuration of the stereoscopic endoscope at the time of a manufacturing inspection in which the right and left connections are correctly made in the above first embodiment.
Figure 8:
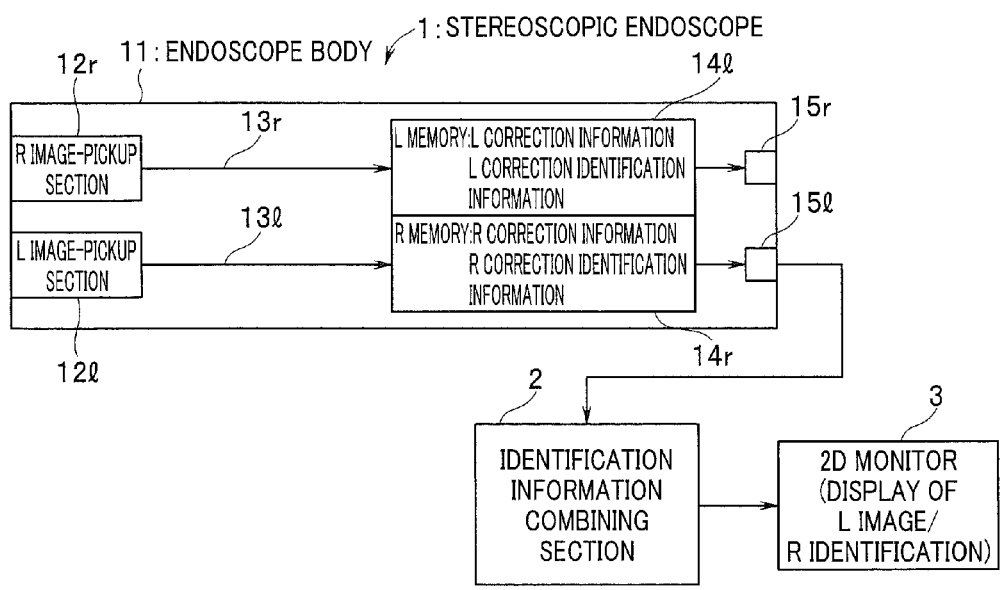
FIG. 8 is a block diagram showing a configuration of the stereoscopic endoscope at the time of a manufacturing inspection in which right and left memories are incorrectly associated with image pickup sections and output sections in the above first embodiment.
Figure 9:
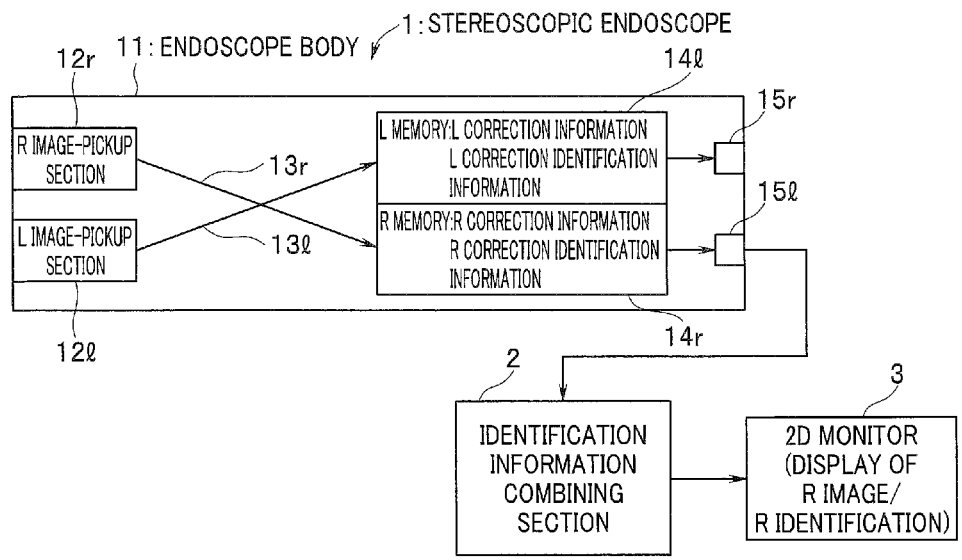
FIG. 9 is a block diagram showing a configuration of the stereoscopic endoscope at the time of a manufacturing inspection in which the right and left output sections are incorrectly associated with the image pickup sections and the memories in the above first embodiment.
Figure 10:
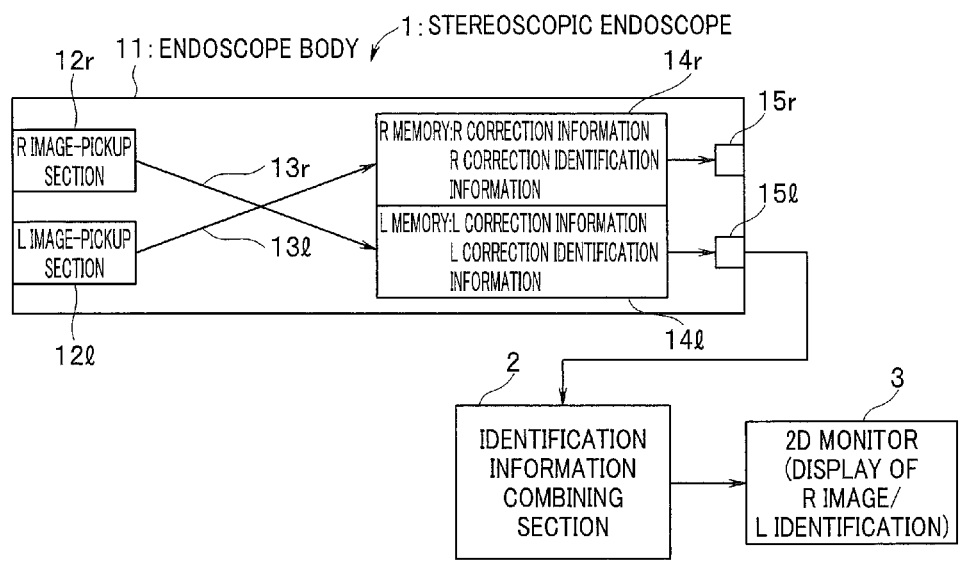
FIG. 10 is a block diagram showing a configuration of the stereoscopic endoscope at the time of a manufacturing inspection in which the right and left memories and output sections are incorrectly associated with the image pickup sections in the above first embodiment.

Next, a flow of a manufacturing inspection will be described along FIG. 12 with reference to FIGS. 7 to 11. FIG. 7 is a block diagram showing a configuration of the stereoscopic endoscope 1 at the time of a manufacturing inspection in which the right and left connections are correctly made; FIG. 8 is a block diagram showing a configuration of the stereoscopic endoscope 1 at the time of a manufacturing inspection in which the right and left memories are incorrectly associated with the image pickup sections and the output sections; FIG. 9 is a block diagram showing a configuration of the stereoscopic endoscope 1 at the time of a manufacturing inspection in which the right and left output sections are incorrectly associated with the image pickup sections and the memories; FIG. 10 is a block diagram showing a configuration of the stereoscopic endoscope 1 at the time of a manufacturing inspection in which the right and left memories and output sections are incorrectly associated with the image pickup sections; FIG. 11 is a diagram showing correct/incorrect classification of association among the right and left output sections, images and pieces of correction information; and FIG. 12 is a flowchart showing a flow of the manufacturing inspection.

Figure 12:
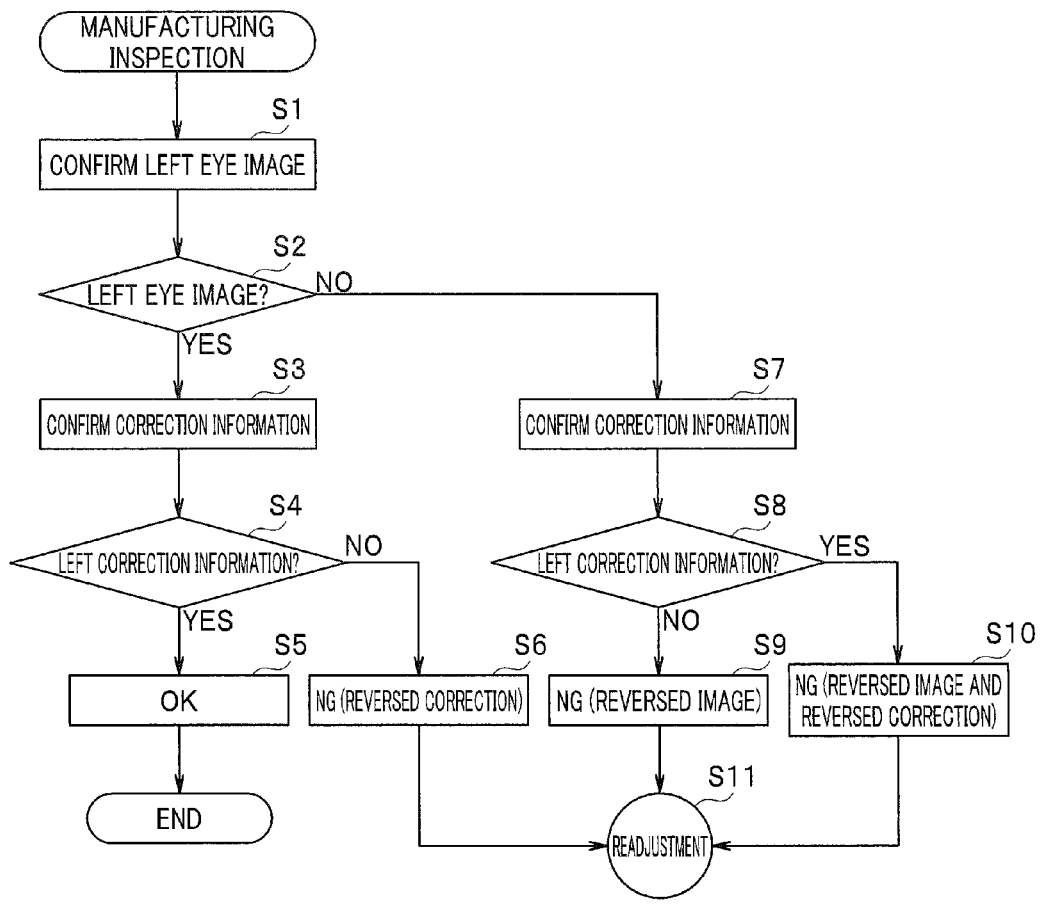
FIG. 12 is a flowchart showing a flow of the manufacturing inspection in the above first embodiment.

When a process shown in FIG. 12 is started, for example, the identification information combining section 2 and the 2D monitor 3 are connected to the L output section 15l, and confirmation of a left eye image, which should be displayed on the screen 3a, is performed, for example, by inserting a finger immediately before a lens of the L image pickup section 12l (step S1). In this case, the image displayed on the screen 3a is a left eye image if the finger is displayed (if the displayed image is covered by the finger and cannot be seen), and is a right eye image if the finger is not displayed (if the displayed image can be seen as it is).

Then, it is judged whether the displayed image is a left eye image or not (step S2).

Here, if it is judged that the displayed image is a left eye image, correction information is confirmed by seeing identification information (for example, the character "R" or the character "L") displayed on the screen 3a (step S3).

It is judged whether the confirmed correction information is L correction information or not (step S4).

Here, if it is judged that the correction information is L correction information, a current state is that a left eye image and L correction identification information are displayed on the screen 3a. Therefore, it is known that the current state is the state shown in FIG. 7 in which the L image pickup section 12l and the L memory 14l are associated with each other and connected to the L output section 15l, the state shown in a case 1 in FIG. 11. That is, it is identified that the current state is a state in which correct connections are made (step S5).

Further, if it is judged at step S4 that the correction information is not L correction information but R correction information, the current state is that a left eye image and R correction identification information are displayed on the screen 3a. Therefore, it is known that the current state is the state shown in FIG. 8 in which the L image pickup section 12l and the R memory 14r are associated with each other and connected to the L output section 15l, the state shown in a case 2 in FIG. 11. That is, it is identified that the current state is a reversed correction state in which, though right and left images outputted from the L output section 15l are correct, pieces of correction information for correcting the images are reversed (step S6).

Furthermore, if it is judged at step S2 that the displayed image is not a left eye image but a right eye image, confirmation of the correction information is performed similarly to step S3 (step S7).

Then, it is judged whether the correction information is L correction information or not (step S8).

Here, if it is judged that the correction information is not L correction information but R correction information, the current state is that a right eye image and R correction identification information are displayed on the screen 3a. Therefore, it is known that the current state is the state shown in FIG. 9 in which the R image pickup section 12r and the R memory 14r are associated with each other and connected to the L output section 15l, the state shown in a case 3 in FIG. 11. That is, it is identified that the current state is a reversed image state in which, though right and left images outputted from the L output section 15l are incorrect, right and left correction information for correcting the images correspond to the right and left images (step S9).

Further, if it is judged at step S8 that the correction information is L correction information, the current state is that a right eye image and L correction identification information are displayed on the screen 3a. Therefore, it is known that the current state is the state shown in FIG. 10 in which the R image pickup section 12r and the L memory 14l are associated with each other and connected to the L output section 15l, the state shown in a case 4 in FIG. 11. It is identified that the current state is a reversed image and reversed correction state in which not only right/left of an image outputted from the L output section 15l is wrong but also right/left of correction information for correcting the image is also opposite to the right/left of the image (step S10).

Thus, if it is confirmed at step S6, S9 or S10 that there is some mistake, a process for re-adjustment corresponding to content of the mistake is performed (step S11), and the manufacturing inspection process is performed again after the re-adjustment. On the other hand, if it is confirmed at step S5 that correct connections are made, the manufacturing inspection process ends.

Note that, though only an output from the L output section 15l is confirmed in the process shown in FIG. 12, an output from the R output section 15r may be confirmed instead. Further, though description has been made above on the case where one of the two memories provided in the stereoscopic endoscope 1 is the R memory 14r, and the other is the L memory 14l, there may be a case where a mistake that R correction information is stored in both of the two memories provided in the stereoscopic endoscope 1 or a mistake that L correction information is stored in both of the two memories occurs. Even such a case can be coped with by performing a process as shown in FIG. 12 for an output from the L output section 15l and further performing a process similar to that shown in FIG. 12 for an output from the R output section 15r. By constructing such an algorithm that 3D video is displayed only in a case of a combination of L and R in the identification information combining section 2, it is possible to detect a mistake because 3D video is not displayed.

Figure 13:
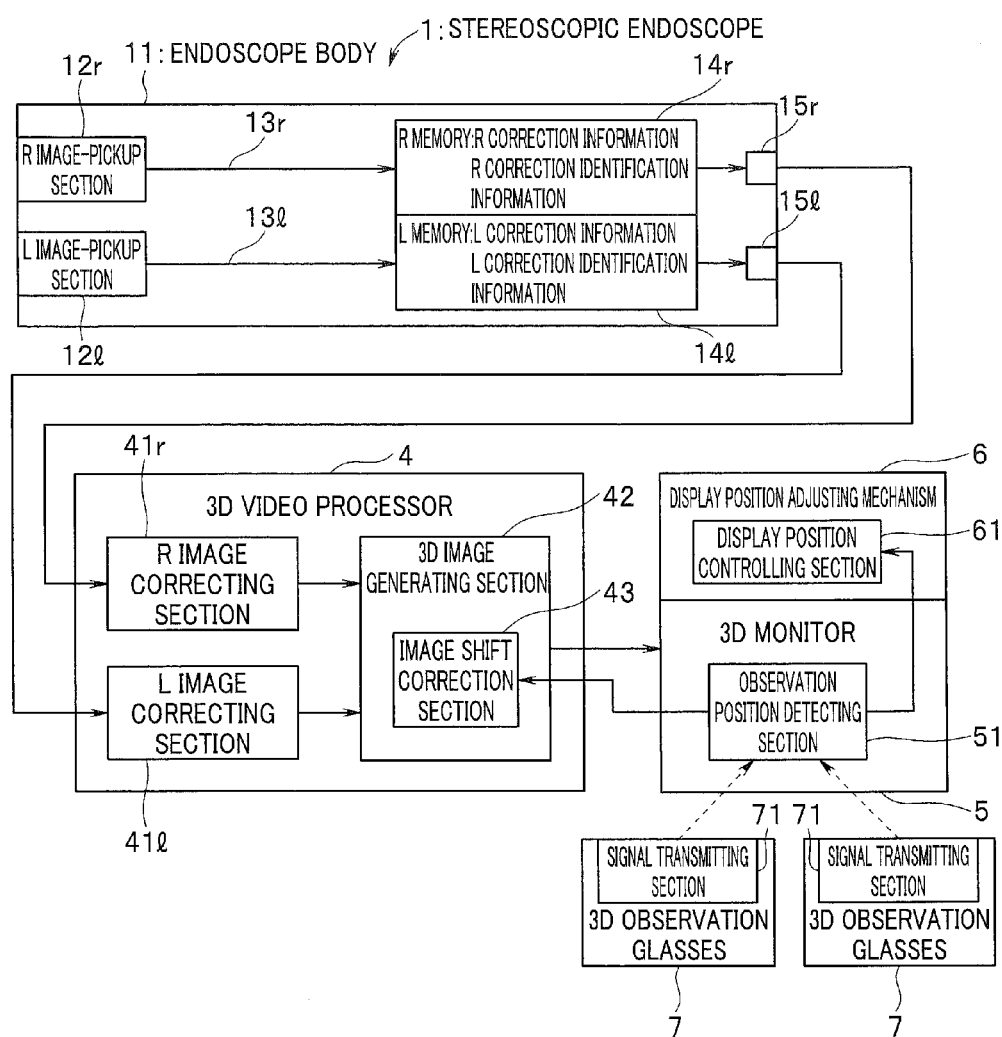
FIG. 13 is a block diagram showing a configuration of the stereoscopic endoscope system when the stereoscopic endoscope which has been correctly adjusted through a manufacturing inspection is used in the above first embodiment.

Next, FIG. 13 is a block diagram showing a configuration of the stereoscopic endoscope system when the stereoscopic endoscope 1 which has been correctly adjusted through the above-described manufacturing inspection is used.

The stereoscopic endoscope system during use after a manufacturing inspection is provided with the stereoscopic endoscope 1, a 3D video processor 4, a 3D monitor 5, a display position adjusting mechanism 6, and one or more pairs of 3D observation glasses 7.

Since the stereoscopic endoscope 1 is correctly adjusted, the R image pickup section 12r is connected to and associated with the R memory 14r via the R signal line 13r and further connected to the R output section 15r, and the L image pickup section 12l is connected to and associated with the L memory 14l via the L signal line 13l and further connected to the L output section 15l. Therefore, the R output section 15r outputs a right eye image and R correction information (or further R correction identification information as necessary), and the L output section 15l outputs a left eye image and L correction information (or further L correction identification information as necessary).

The 3D video processor 4 is a video processor which is provided with an R image correcting section 41r to which the R output section 15r is connected, an L image correcting section 41l to which the L output section 15l is connected, and a 3D image generating section 42, and which generates a 3D right eye image obtained by correcting a right eye image with R correction information and a 3D left eye image obtained by correcting a left eye image with L correction information.

The R image correcting section 41r performs correction of performing cutout of an inputted right eye image based on inputted R correction information, and the L image correcting section 41l performs correction of performing cutout of an inputted left eye image based on inputted L correction information.

The 3D image generating section 42 generates a 3D right eye image, which is a right eye image for stereoscopic observation, based on the right eye image corrected by the R image correcting section 41r and generates a 3D left eye image, which is a left eye image for stereoscopic observation, based on the left eye image corrected by the L image correcting section 41l.

The 3D image generating section 42 is provided with an image shift correction section 43 and is adapted to increase or decrease a convergence angle at time of observing a stereoscopic image by performing image shift of the right eye image corrected by the R image correcting section 41*r* and performing image shift of the left eye image corrected by the L image correcting section 41*l* so as to perform control for emphasizing or reducing a stereoscopic effect of a 3D image.

Note that the 3D video processor 4 may be configured so that it includes the function of the identification information combining section 2 described above, and the 2D monitor 3 can be connected. In this case, a normal mode and an inspection mode are provided so that the 3D monitor 5 is connected to perform stereoscopic observation in the normal mode, and the 2D monitor 3 is connected to perform a manufacturing inspection and the like as described above in the inspection mode.

The 3D monitor 5 displays a stereoscopic image based on a 3D right eye image and a 3D left eye image from the 3D video processor 4. The 3D monitor 5 is provided with an observation position detecting section 51 which detects a position of an observer relative to the 3D monitor 5 and acquires an observation center position based on the detected position of the observer. Here, information about the position of the observer detected by the observation position detecting section 51 includes information about a distance and direction to the observer when the 3D monitor 5 is a base position. Therefore, information about the acquired observation center position also includes information about a distance and direction to the observation center position when the 3D monitor 5 is the base position.

Then, in the case of a single observer, the observation position detecting section 51 causes a detected position of the observer to be the observation center position. In the case of a plurality of observers, the observation position detecting section 51 causes, for example, a mean value (a simple average, a weighted average or the like) of detected positions of the plurality of observers to be the observation center position (otherwise, the observation center position may be acquired by a statistical method such as excluding outliers from calculation targets, instead of the average calculation).

Note that, though the observation position detecting section 51 is provided in the 3D monitor 5 here, the observation position detecting section 51 may be arranged at a position other than the 3D monitor 5 if necessary information can be acquired.

The image shift correction section 43 described above performs a process for performing image shift of a 3D right eye image and a 3D left eye image so that a convergence angle is appropriate when the 3D monitor 5 is seen from the observation center position. Note that, though the image shift correction section 43 is provided in the 3D video processor 4 in the above description, this is not limiting, and the image shift correction section 43 may be provided at other position. For example, the image shift correction section 43 may be provided in the 3D monitor 5.

Note that the 3D monitor 5 and the 2D monitor 3, which is also used during a manufacturing inspection, may be realized by switching between modes of one monitor. In this case, it is preferred to make a program so that the right/left pieces of identification information described above are displayed when the one monitor functions as the 2D monitor 3. Further, when the one monitor functions as the 3D monitor 5 also, it is possible to display the right/left pieces of identification information. If such an operation is performed, it is preferred to display the left identification information and the right identification information in an area at a left end of a screen 5*a* (see FIG. 19) which is not combined with a 3D right eye image if the area exists and an area at a right end of the screen 5*a* which is not combined with a 3D left eye image if the area exists, respectively (because displayed object areas of the 3D right eye image and the 3D left eye image do not necessarily correspond to each other but may differ from each other). Further, it is preferred to be able to switch between display/non-display of the right/left pieces of identification information as desired by a switch or the like provided on an operation portion side of the stereoscopic endoscope 1 at hand or a switch or the like provided on the 3D video processor 4.

The display position adjusting mechanism 6 changes a position of the screen 5*a* of the 3D monitor 5 and includes a display position controlling section 61, and a drive mechanism such as a motor to be described later.

Further, the display position controlling section 61 causes the display position adjusting mechanism 6 to change the position of the screen of the 3D monitor 5 so that the observation center position comes close to a center of a visual field $\Omega$ (see FIGS. 17 and 18), which is a range appropriate for stereoscopy of the 3D monitor 5 (that is, so that the observation center position comes as close to the center of the visual field $\Omega$ as possible even when it is not possible to cause the observation center position to be the center of the visual field $\Omega$, though it is preferable that the observation center position is the center). Note that, though the display position controlling section 61 is provided in the display position adjusting mechanism 6 here, a configuration in which the display position controlling section 61 is provided outside the display position adjusting mechanism 6 is also possible.

One or a plurality of pairs of 3D observation glasses 7 are provided in the stereoscopic endoscope system. The pair of 3D observation glasses 7 is such that enables stereoscopic observation according to a display system of the 3D monitor 5 when worn by an observer. Specifically, the pair of 3D observation glasses 7 becomes a pair of polarizing glasses when the 3D monitor 5 is a polarization type monitor and becomes a pair of liquid crystal shutter glasses when the 3D monitor 5 is an active shutter type monitor.

In the present embodiment, the pair of 3D observation glasses 7 adopts a configuration of being provided with a signal transmitting section 71 which transmits a signal receivable by the observation position detecting section 51. The observation position detecting section 51 described above is adapted to detect a position of an observer based on a signal received from the signal transmitting section 71. Especially, a signal transmitted by the signal transmitting section 71 of the present embodiment includes a signal capable of identifying an individuality of the pair of 3D observation glasses 7. In the case of a plurality of observers, the observation position detecting section 51 weights the positions of the observers according to detected positions of the observers based on which pair of 3D observation glasses 7 a signal is received from, and then causes a mean value of calculated positions of the plurality of observers to be the observation center position.

However, it is not indispensable that the pair of 3D observation glasses 7 is provided with the signal transmitting section 71. If the pair of 3D observation glasses 7 is not provided with the signal transmitting section 71, the observation position detecting section 51 may be such that detects a position of an observer by performing analysis of an image obtained by picking up an image of an observer side from a 3D monitor 5 side (for example, by performing face detection and performing distance detection based on contrast AF for a detected face, direction detection based on a position of the face in the image and an image pickup angle of view, and the like).

Figure 14:
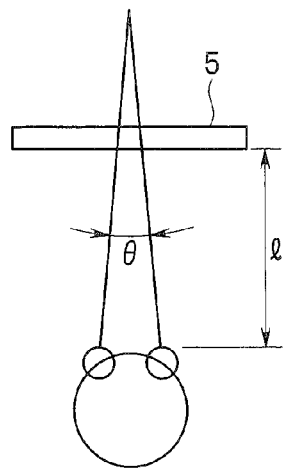
FIG. 14 is a diagram showing a convergence angle when there is a certain distance between a 3D monitor and an observer in the above first embodiment.
Figure 15:
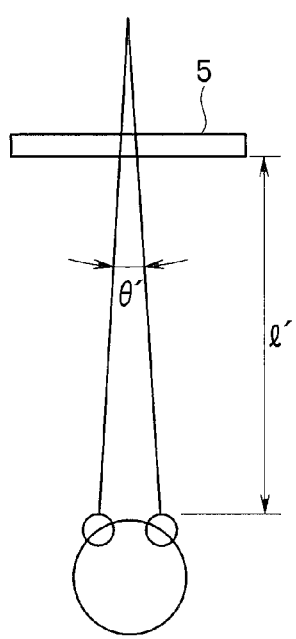
FIG. 15 is a diagram showing a convergence angle when there is another distance between the 3D monitor and the observer in the above first embodiment.

Next, FIG. 14 is a diagram showing a convergence angle when there is a certain distance between the 3D monitor 5 and an observer; and FIG. 15 is a diagram showing a convergence angle when there is another distance between the 3D monitor 5 and the observer.

When the convergence angle at time when the distance between the 3D monitor 5 and the observer as shown in FIG. 14 is l is indicated by θ, the convergence angle at time when the distance between the 3D monitor 5 and the observer becomes l' becomes θ' as shown in FIG. 15. That is, as the distance between the 3D monitor 5 and the observer changes in the stereoscopic endoscope system, the convergence angle changes. Change in the convergence angle is felt, for example, as change in a feeling of depth in stereoscopy by the observer.

Therefore, in the stereoscopic endoscope system, image shift is performed by the image shift correction section 43 so that an observer within some distance range can appropriately feel the feeling of depth in stereoscopy. Such an area appropriate for performing stereoscopic observation is assumed as the visual field Ω.

When the observer is beyond the visual field Ω of the 3D monitor 5, for example, a crosstalk (such as observing not only a 3D left eye image but also a part of a 3D right eye image by a left eye and observing not only the 3D right eye image but also a part of the 3D left eye image by a right eye, and the like) may occur, and it may be difficult to perform stereoscopy. In the case of one observer, it is relatively easy for the observer to adjust the position of the 3D monitor 5 in advance so that he can easily perform observation. In the case where a plurality of observers simultaneously observe one 3D monitor 5, however, there may be a case where it is not possible to perform stereoscopy in an optimum state depending on a positional relationship between the observers and the 3D monitor 5. Moreover, it is difficult to objectively judge whether an observer is within the visual field Ω of a monitor, and there is not any other appropriate method than making a confirmation by actually seeing a stereoscopic image. Further, especially in the case of a plurality of observers, it is also conceivable that some observers move and go beyond the visual field Ω or return into the visual field Ω again. Further, in a surgical environment, an observer, who is a clean person, cannot directly touch a monitor which is not clean. Therefore, a third person, who is an unclean person, has to adjust a position of the monitor, and, therefore, there is a problem that adjustment tends to be complicated.

Figure 17:
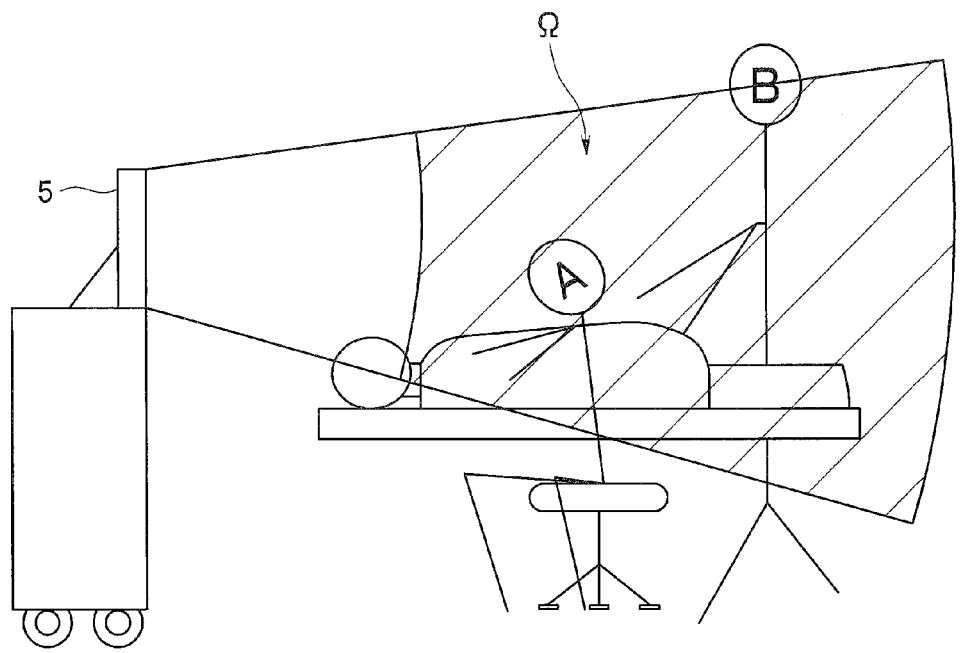
FIG. 17 is a side view showing a positional relationship between a visual field of the 3D monitor and two of the observers shown in FIG. 16 in the above first embodiment.
Figure 18:
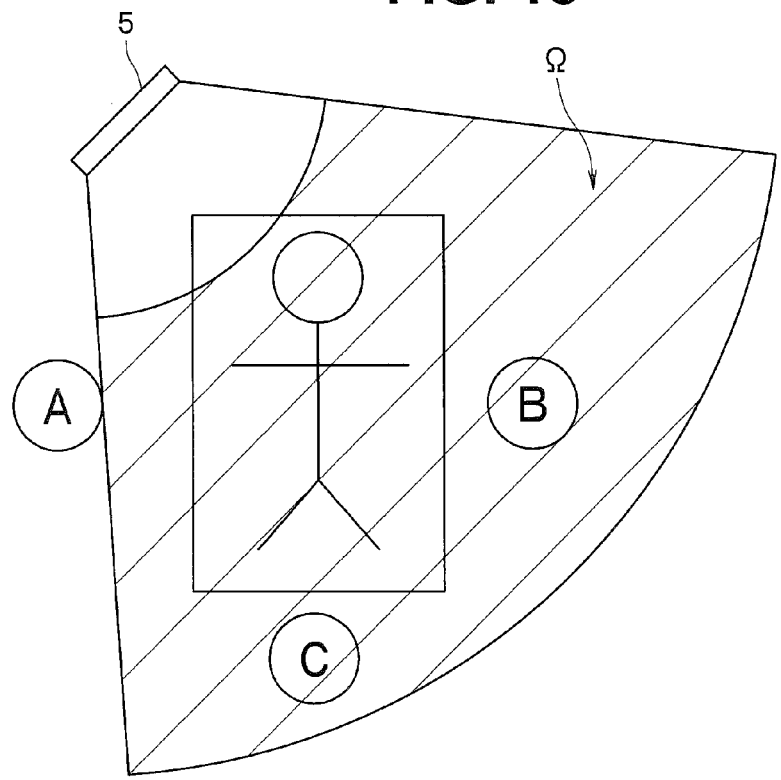
FIG. 18 is a plan view showing a positional relationship between the visual field of the 3D monitor and the three observers in the above first embodiment.

An example of such a case will be described with reference to FIGS. 16 to 18.

Figure 16:
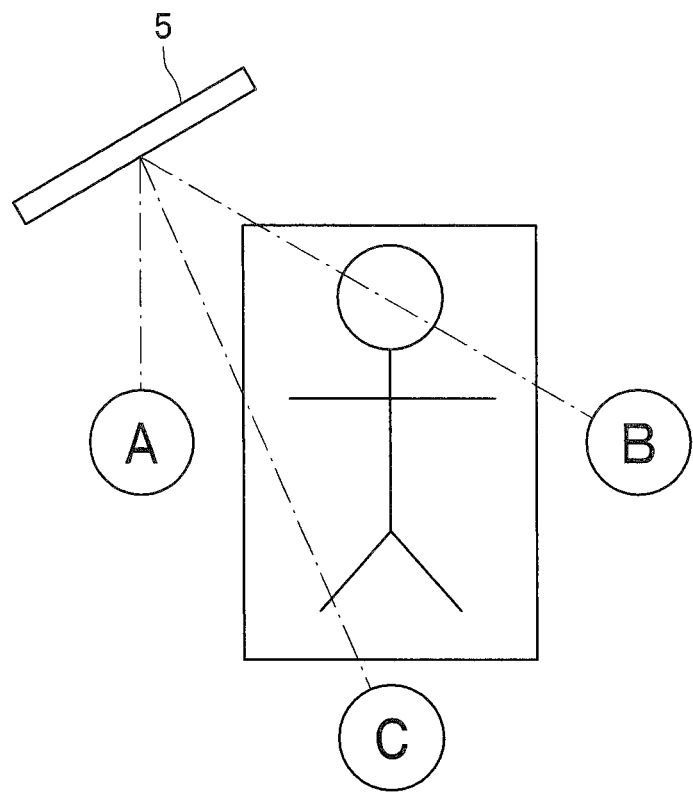
FIG. 16 is a plan view showing a state that there are three observers in an endoscopy using the stereoscopic endoscope of the above first embodiment.

FIG. 16 is a plan view showing a state that there are three observers in an endoscopy using the stereoscopic endoscope; FIG. 17 is a side view showing a positional relationship between the visual field Ω of the 3D monitor and two of the observers shown in FIG. 16; and FIG. 18 is a plan view showing a positional relationship between the visual field Ω of the 3D monitor and the three observers.

As shown in FIG. 16, it is assumed that there are observers A to C who observe the 3D monitor 5, around a subject. When this is laterally seen, the state is, for example, as shown in FIG. 17, and eyes of the standing observer B are positioned beyond a border of the visual field Ω. On the other hand, the observer A, who is sitting, appears to be within the visual field Ω in FIG. 17. When seen from above, however, he is positioned beyond the visual field Ω as shown in FIG. 18.

The stereoscopic endoscope system of the present embodiment is adapted to, in such a case, automatically perform two kinds of adjustments: adjustment of the convergence angle by performing image shift and position adjustment related to height, direction and the like of the screen 5a of the 3D monitor 5.

Figure 20:
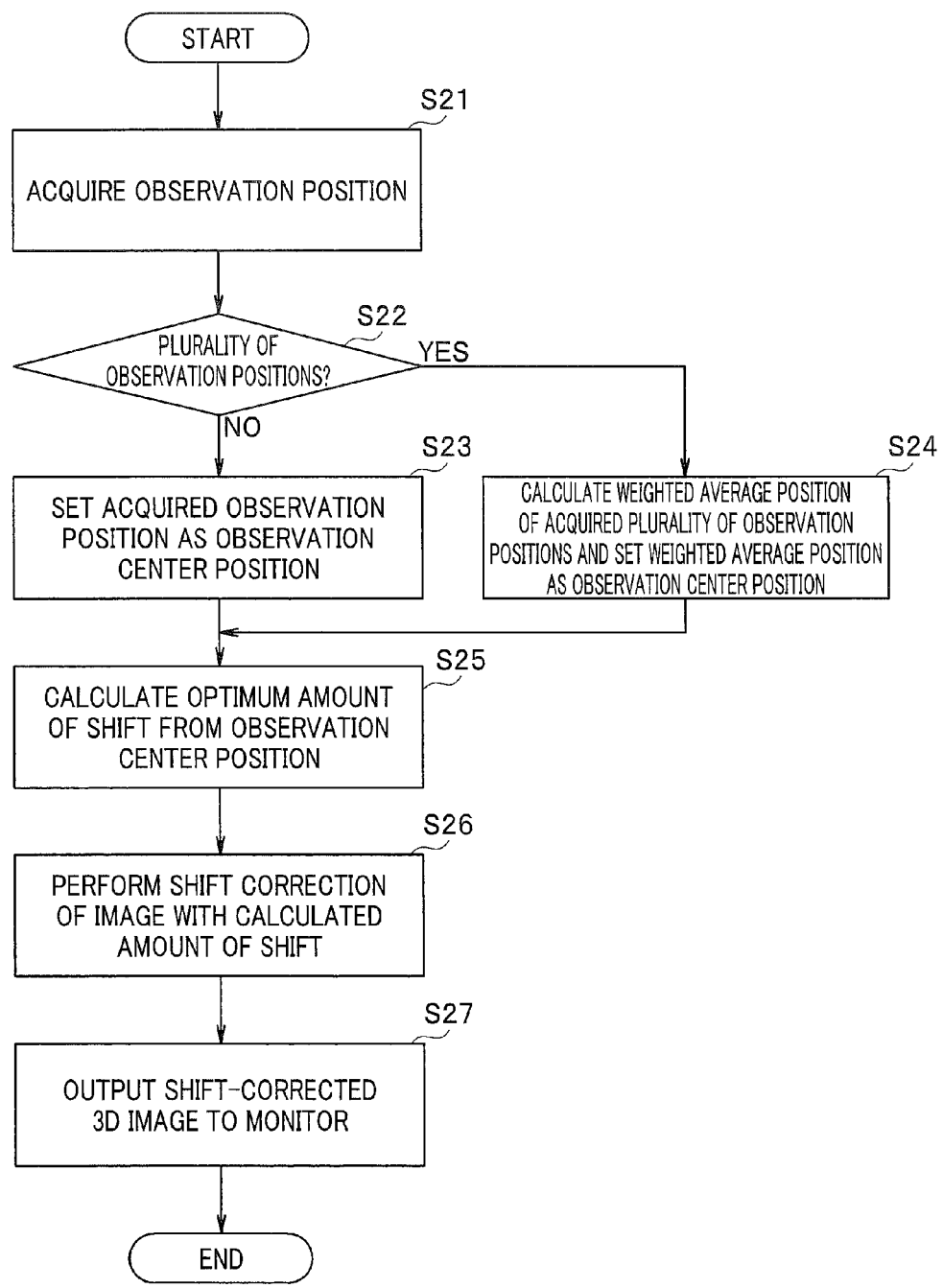
FIG. 20 is a flowchart showing a flow of a convergence angle adjustment process in the above first embodiment.

First, the adjustment of the convergence angle, which is a first adjustment, is performed by the image shift correction section 43 based on an observation center position acquired by the observation position detecting section 51. FIG. 20 is a flowchart showing a flow of a convergence angle adjustment process.

When the process starts, the observation position detecting section 51 receives a signal transmitted by the signal transmitting section 71 of the pair of 3D observation glasses 7 to acquire a position of an observer (step S21).

Then, the observation position detecting section 51 judges whether it has acquired a plurality of positions of observers or not (step S22).

Here, if the observation position detecting section 51 has acquired the one position of the observer, the observation position detecting section 51 sets the detected position of the observer as the observation center position (step S23).

Further, if it is judged at step S22 that a plurality of positions of observers have been acquired, the observation position detecting section 51 calculates, for example, a weighted average position of the detected plurality of positions of the observers and sets the weighted average position as the observation center position (step S24). Here, weight used to calculate a weighted average is set in advance for each individual pair of 3D observation glasses 7 or manually set each time each individual pair of 3D observation glasses 7 is used. Weighting of each observer is performed based on a signal capable of identifying an individual from the pair of 3D observation glasses 7.

Next, the image shift correction section 43 calculates an amount of shift mainly based on information about a distance from the 3D monitor 5 to the observation center position (or based not only on the distance information but also information about a direction of the observation center position seen from the 3D monitor 5) so that an optimum convergence angle can be obtained at the observation center position set by the process of step S23 or S24 (step S25).

Then, the image shift correction section 43 performs image shift of a 3D right eye image and a 3D left eye image based on the calculated amount of shift (step S26).

The 3D video processor 4 outputs the shift-corrected 3D images to the 3D monitor 5, and the 3D monitor 5 performs stereoscopic display of the images (step S27), and the process ends.

Figure 19:
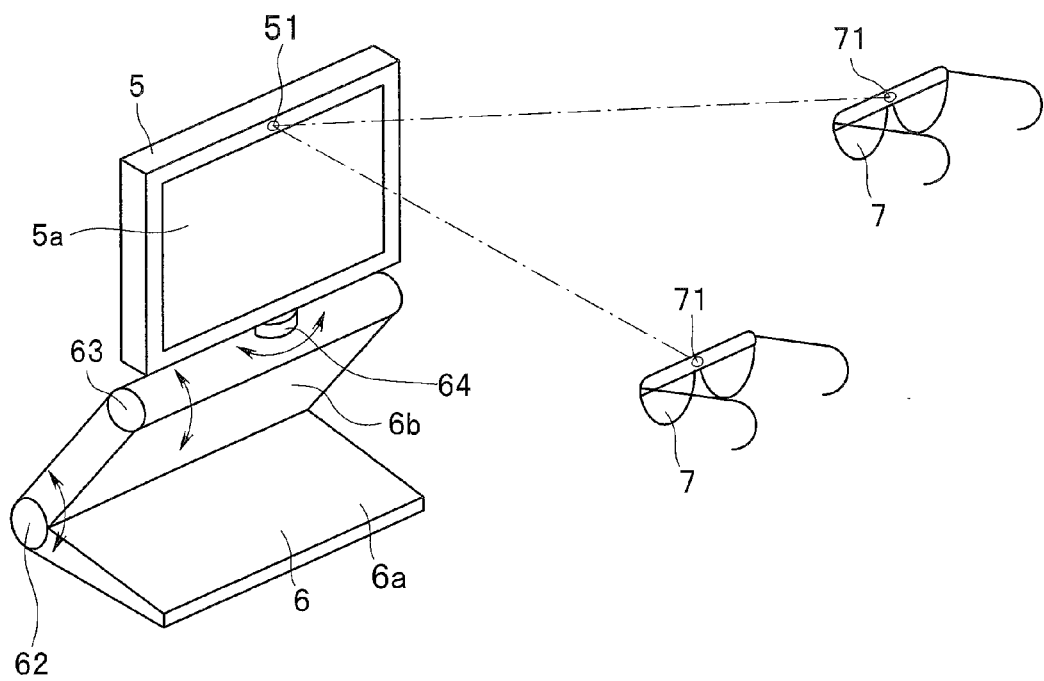
FIG. 19 is a perspective view showing a configuration example of a display position adjusting mechanism in the above first embodiment.

Next, the position adjustment of the screen 5a of the 3D monitor 5, which is a second adjustment, is performed by the display position adjusting mechanism 6 based on the observation center position acquired by the observation position detecting section 51. Here, FIG. 19 is a perspective view showing a configuration example of the display position adjusting mechanism 6.

The display position adjusting mechanism 6 is provided with, for example, a base portion 6a to be placed on a table or the like; a first hinge 62 which is horizontally provided on an edge portion of one end of the base portion 6a and which is rotatable by a first motor or the like; a support portion 6b configured to be rotatable relative to the base portion 6a via the first hinge 62; a second hinge 63 which is horizontally provided on an upper end portion of the support portion 6b and which is rotatable by a second motor or the like; and a third hinge 64 which is provided on a central part of the second hinge 63 and which is rotatable in a direction orthogonal to the second hinge 63 by a third motor or the like.

The first hinge 62 rotates by control of the display position controlling section 61 (see FIG. 13) and moves the 3D monitor 5 (therefore, the screen 5a) in a vertical direction (upward and downward along a gravity direction).

The second hinge 63 rotates by control of the display position controlling section 61 and adjusts an elevation angle/depression angle (that is, so-called pitch) of the 3D monitor 5 (therefore, the screen 5a).

The third hinge 64 rotates by control of the display position controlling section 61 and adjusts right and left angles (that is, so-called yaw) of the 3D monitor 5 (therefore, the screen 5a). The 3D monitor 5 is attached via the third hinge 64.

Note that, though so-called roll of the 3D monitor 5 is not adjusted here because necessity of the adjustment is low, the 3D monitor 5 may be, of course, configured such that the roll is adjustable if it is necessary for some reason.

Figure 21:
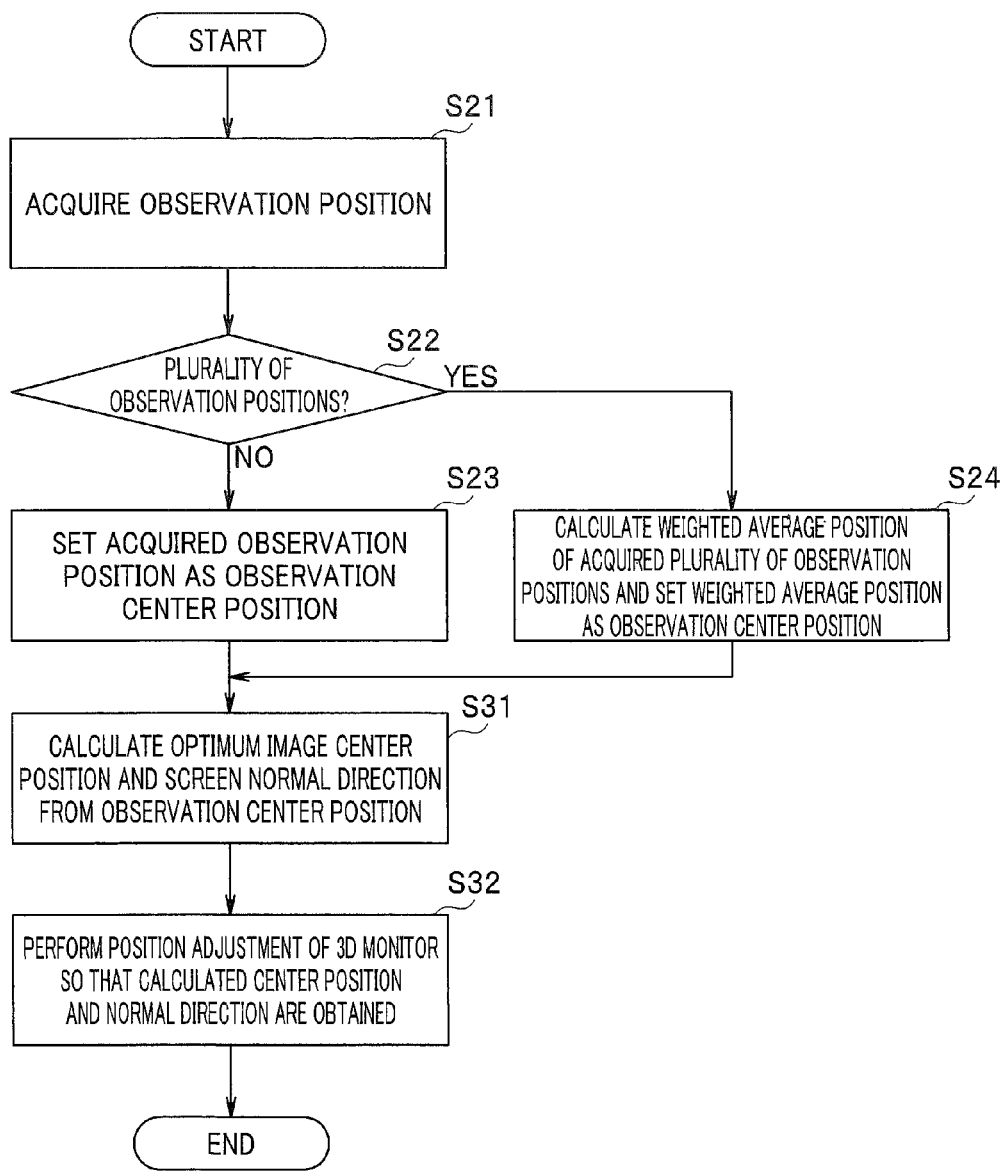
FIG. 21 is a flowchart showing a flow of a process for position adjustment of a screen of the 3D monitor in the above first embodiment.

FIG. 21 is a flowchart showing a flow of a process for position adjustment of the screen 5a of the 3D monitor 5.

When the process starts, the observation center position is set by performing the process of steps S21 to S24 as described with reference to FIG. 20.

Next, the display position controlling section 61 calculates, for example, the center position and normal direction of the screen 5a so that the observation center position set by the process of step S23 or S24 is close to the center of the visual field Ω, which is a range appropriate for stereoscopy of the 3D monitor 5 (see FIGS. 17 and 18), that is, so that the observation center position corresponds to the center of the visual field Ω if the observation center position is inside a movable range, and comes to a position which is the closest to the center of the visual field Ω if the observation center position is outside the movable range (step S31).

Then, the display position controlling section 61 drives the first to third motors and the like to rotate the first to third hinges 62 to 64 to perform position adjustment of the 3D monitor 5 so that the center position and normal direction of the screen 5a correspond to the center position and normal direction obtained by calculation of step S31 (step S32), and the process ends.

Note that, if it is not possible to cause the observation center position to correspond to the center of the visual field Ω at step S31 because the observation center position is outside the movable range, a message or the like may be displayed indicating that the direction and height of the 3D monitor 5 are to be manually adjusted.

Further, it is also possible to judge, for each of all observers, whether he is inside or outside the visual field Ω and, if any observer is outside the visual field Q, display a message or the like informing to that effect.

Further, though a single 3D monitor is used in the present embodiment, a plurality of 3D monitors may be used. In that case, a mechanism, a program or the like may be provided which is for weighting a certain particular observer so that a position of each monitor is adjusted or adjusting positions of the monitors so that a particular observer can perform observation with a central value of a visual field as far as possible. Note that, in the case of performing observation with a plurality of 3D monitors, it is preferred to adopt the polarization type because it is difficult to synchronize right and left signals among the 3D monitors of the active shutter type.

By the way, if the pair of 3D observation glasses 7 is, for example, a pair of polarizing glasses, an amount of passing light decreases because light passing through polarizing filters fitted to right and left lens portions is limited to polarized light in a particular direction. If the pair of 3D observation glasses 7 is a pair of liquid crystal shutter glasses, the amount of passing light decreases because a transit time period during which light passes through the right and left lens portions is restricted. Therefore, when observation is performed with use of the pair of 3D observation glasses 7, a field of view becomes dark. If it is the 3D monitor 5 that is to be observed, luminance of the screen 5a can be increased to cope with the darkness. In a case of observing a portion other than the screen 5a which is illuminated with ambient light, the field of view inevitably becomes dark.

Figure 22:
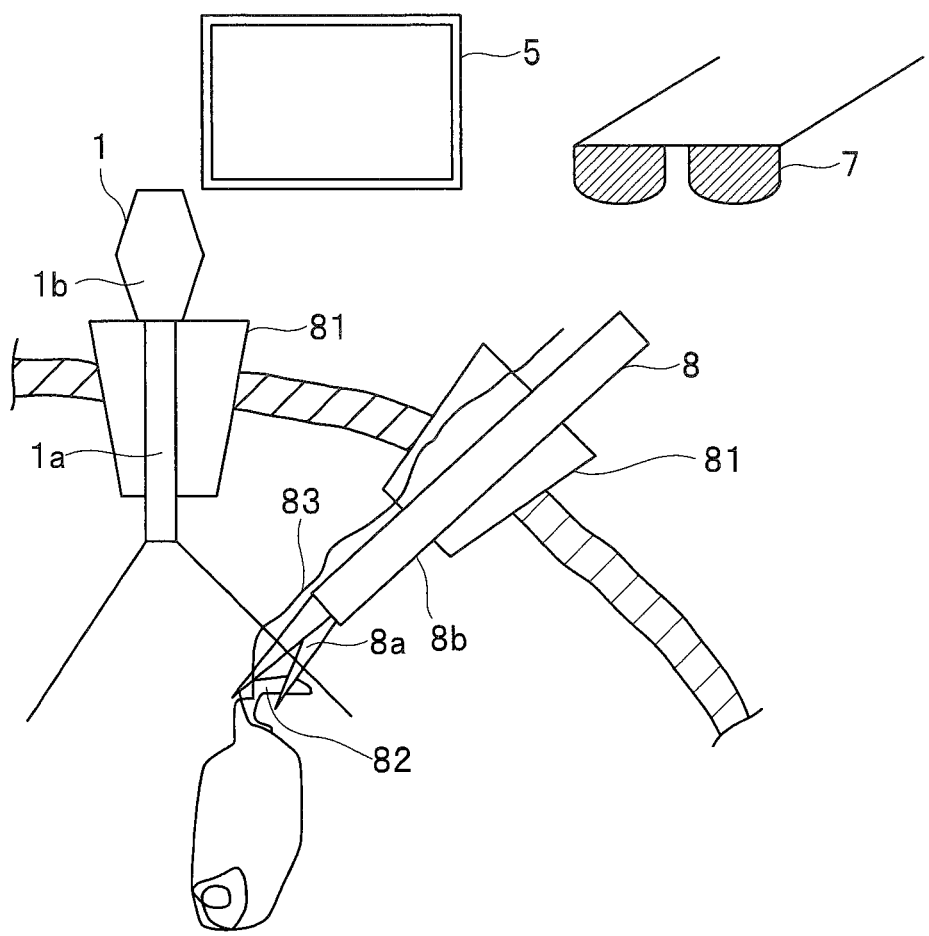
FIG. 22 is a diagram showing that suturing is being performed in an abdominal cavity while observation is being performed with the stereoscopic endoscope in the above first embodiment.
Figure 23:
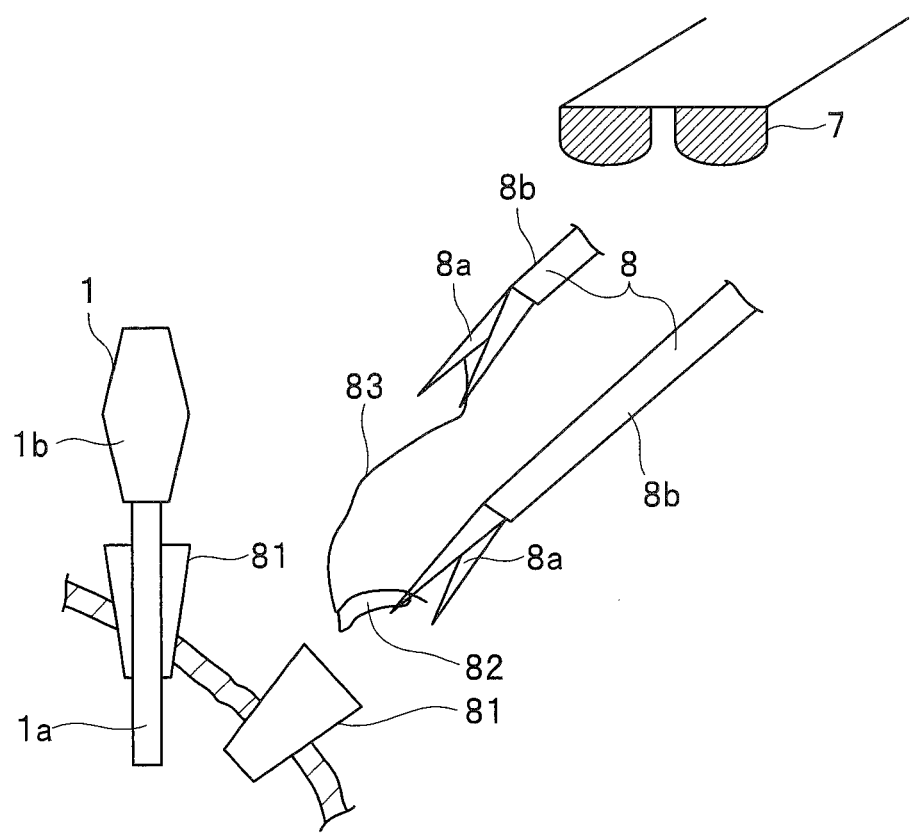
FIG. 23 is a diagram showing that a needle is taken out from the inside of the abdominal cavity, and a thread attached to the needle is cut at hand in the above first embodiment.

Description will be made on a case where the stereoscopic endoscope 1 is a stereoscopic laparoscope as a specific example, with reference to FIGS. 22 and 23. Here, FIG. 22 is a diagram showing that suturing is being performed in an abdominal cavity while observation is being performed with the stereoscopic endoscope 1; and FIG. 23 is a diagram showing that a needle is taken out from the inside of the abdominal cavity, and a thread attached to the needle is cut at hand.

In an abdominal region of a subject, the stereoscopic endoscope 1 and a treatment instrument 8, such as a forceps, are inserted in the abdominal cavity via a trocar 81 and another trocar 81, respectively.

An operation portion 1b of the stereoscopic endoscope 1 on a hand side is outside the trocar 81, and an insertion portion 1a on a distal end side is inserted in the abdominal cavity through the trocar 81.

Further, the treatment instrument 8 is configured such that a treatment portion 8a is provided on a distal end side of an insertion portion 8b. The insertion portion 8b passes through the trocar 81, and the treatment portion 8a on the distal end side is inserted in the abdominal cavity.

As described above, FIG. 22 shows that suturing is being performed in the abdominal cavity with use of a needle 82 (with a thread 83) held by the treatment portion 8a of the treatment instrument 8 while stereoscopic observation is being performed by the stereoscopic endoscope 1.

Next, when the thread 83 attached to the needle 82 is cut after suturing in the abdominal cavity has been performed, the needle 82 held by the treatment instrument 8 is taken out from the trocar 81 to do work at hand, as shown in FIG. 23.

However, when the pair of 3D observation glasses 7 is still worn at the time of cutting the thread 83 attached to the needle 82 with another treatment instrument 8, it becomes dark around hands because the amount of light reaching the eyes of the observer decreases as described above, and it becomes difficult to do the work.

Though the observer wants to remove the pair of 3D observation glasses 7 to perform observation brightly, a clean person such as a surgeon cannot touch the pair of 3D observation glasses 7 because the pair of 3D observation glasses 7 is, for example, in an unsterile state.

Further, though it is conceivable to use a separate external illumination as another method, the external illumination is also in the unsterile state similarly to the pair of 3D observation glasses 7. Therefore, it is required to ask another person to do the work of applying external illumination when necessary and turning off the external illumination when it becomes unnecessary, which causes work to be very complicated and leads to delay of a surgical procedure.

Further, it is also possible to take out the stereoscopic endoscope 1 from the trocar 81 and use illuminating light emitted from the distal end of the stereoscopic endoscope 1 as illumination for hands, it is not preferred that the sutured portion is out of the field of view when another treatment instrument is in the abdominal cavity and suturing is being performed.

Figure 24:
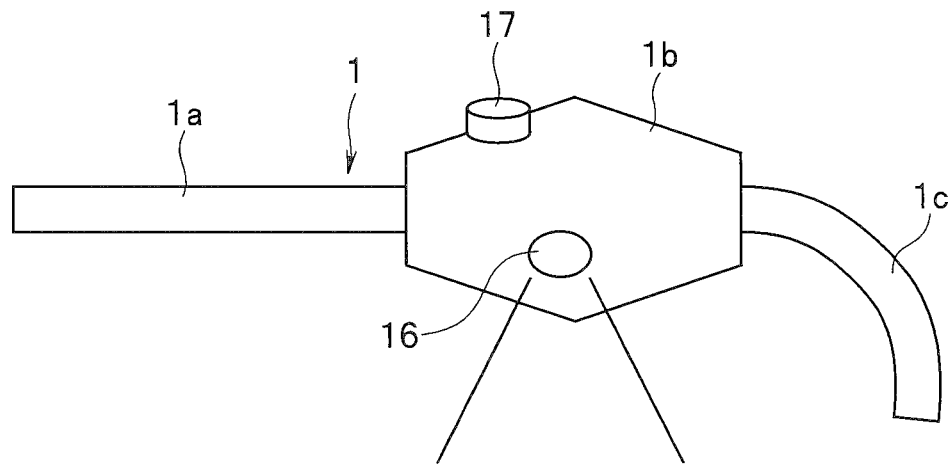
FIG. 24 is a diagram showing a configuration in which a hand illuminating portion is provided on a side face of an operation portion of the stereoscopic endoscope in the above first embodiment.
Figure 25:
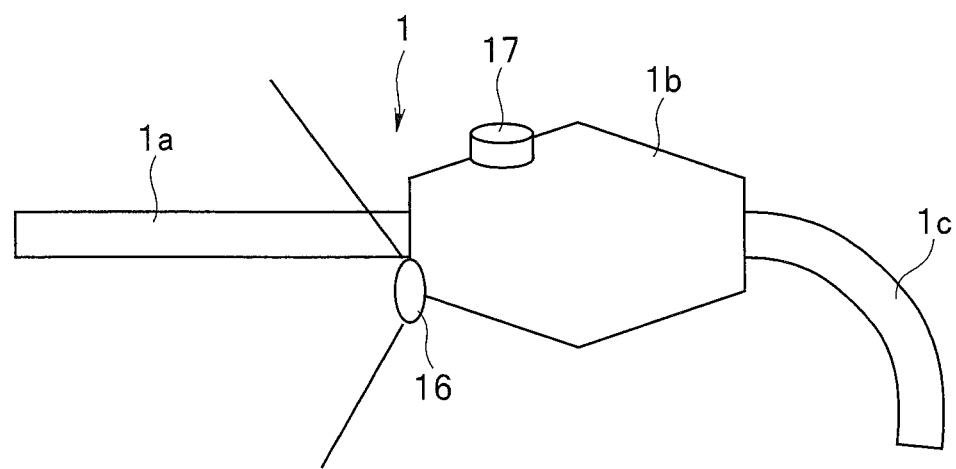
FIG. 25 is a diagram showing a configuration in which the hand illuminating section is provided on a connection face between the operation portion and an insertion portion of the stereoscopic endoscope in the above first embodiment.
Figure 28:
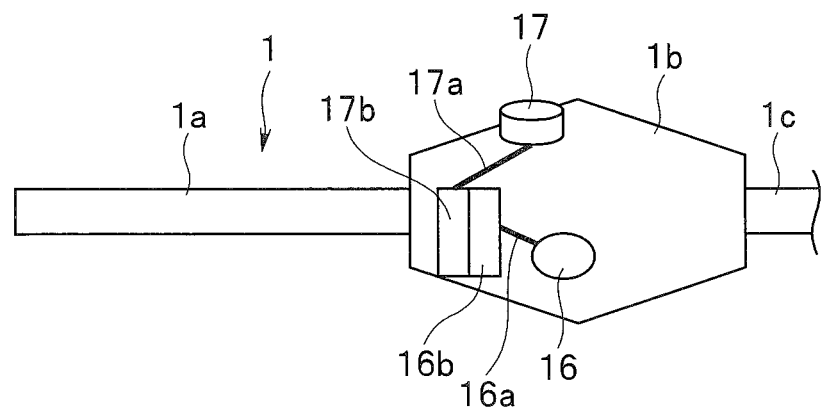
FIG. 28 is a diagram showing a configuration example in which the light emission source is provided on the hand illuminating section to perform control within the operation portion of the stereoscopic endoscope in the above first embodiment.
Figure 29:
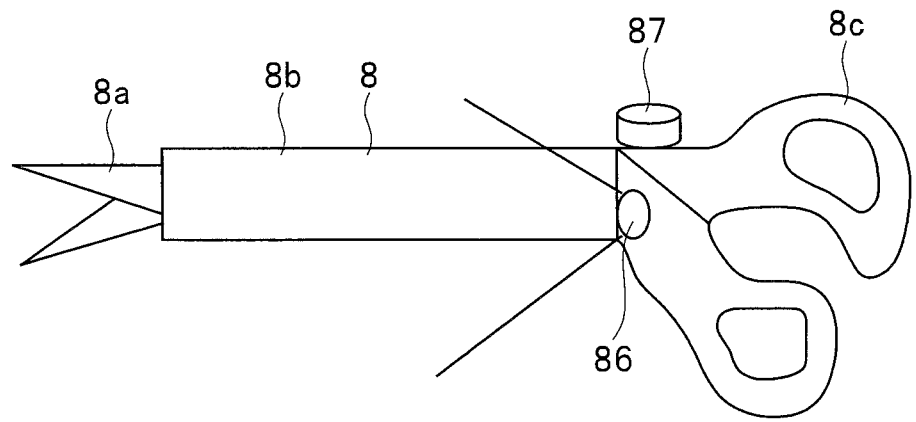
FIG. 29 is a diagram showing a configuration example in which a hand illuminating section is provided on a hand side of a treatment instrument in the above first embodiment.

A configuration made in view of such a viewpoint will be described with reference to FIGS. 24 to 29. FIG. 24 is a diagram showing a configuration in which a hand illuminating section 16 is provided on a side face of the operation portion 1*b* of the stereoscopic endoscope 1; FIG. 25 is a diagram showing a configuration in which the hand illuminating section 16 is provided on a connection face between the operation portion 1*b* and the insertion portion 1*a* of the stereoscopic endoscope 1; FIG. 26 is a diagram showing a configuration example in which a light source of the hand illuminating section 16 is also used as a light source of illuminating light to a distal end portion of the insertion portion 1*a* of the stereoscopic endoscope 1; FIG. 27 is a diagram showing a configuration example in which a light emission source is provided on the hand illuminating section 16 to perform control via a 3D video processor 4A; FIG. 28 is a diagram showing a configuration example in which the light emission source is provided on the hand illuminating section 16 to perform control within the operation portion 1*b* of the stereoscopic endoscope 1; and FIG. 29 is a diagram showing a configuration example in which a hand illuminating section 86 is provided on a hand side of the treatment instrument 8.

First, FIG. 24 shows a configuration example in which the hand illuminating section 16 is provided on the side face of the operation portion 1*b* in the stereoscopic endoscope 1, and, further, a hand illuminating switch 17 for switching on/off of the hand illuminating section 16 is provided on the operation portion 1*b*.

Further, FIG. 25 shows a configuration example in which, though arrangement of the hand illuminating switch 17 is similar to that of FIG. 24, the hand illuminating section 16 is provided on a face on a distal end side of the operation portion 1*b* of the stereoscopic endoscope 1 (the face of connection with the insertion portion 1*a*).

Next, as shown in FIG. 26, a cable 1*c*, such as a universal cable and an illumination cable, is provided being extended from the hand side of the stereoscopic endoscope 1, and is connected to a light source device 9 or a video processor or the like which includes a light source device via a connector 1*d*. The hand illuminating section 16 shown in FIG. 26 is in a configuration example in which a part of a light guide 18 which is configured, for example, with an optical fiber bundle and which transmits illuminating light from the light source device 9 to a distal end side of the insertion portion 1*a* is branched to be a branched light guide 18*a*, and light is emitted via an illuminating window to be used as illuminating light for hands. Therefore, the hand illuminating section 16 is provided, for example, with an illumination cover openable and closable relative to the illuminating window, and on/off of illumination is switched by operating the illumination cover.

On the other hand, in the configuration example shown in FIG. 27, an operation input from the hand illuminating switch 17 is inputted to the 3D video processor 4A via a signal line 17*a* arranged in the cable 1*c*. When an illumination-on signal is inputted from the hand illuminating switch 17, the 3D video processor 4A supplies power to the hand illuminating section 16 via a power line 16*a* arranged in the cable 1*c*. The hand illuminating section 16 is configured, including a lamp such as an LED as a light emitting source, and emits light when power is supplied. On the other hand, when an illumination-off signal is inputted from the hand illuminating switch 17, the 3D video processor 4A shuts down power supply to the hand illuminating section 16, and light emission stops.

FIG. 28 shows a configuration example in which light emission control of the hand illuminating section 16 according to an operation of the hand illuminating switch 17 is performed in the operation portion 1*b*. That is, a control board 17*b* and a power source 16*b* are further provided in the operation portion 1*b*, and the signal line 17*a* from the hand illuminating switch 17 and the power line 16*a* from the power source 16*b* are connected to the control board 17*b* and the hand illuminating section 16, respectively. Note that it is similar to the configuration example of FIG. 27 that the hand illuminating section 16 is configured including a lamp such as an LED. By such a configuration, an illumination on/off signal from the hand illuminating switch 17 is inputted to the control board 17*b* so that the control board 17*b* controls the power source 16*b* to control on/off of power supply to the hand illuminating section 16, that is, emission/stop of illuminating light for hands.

More generally speaking, the some examples described above are configuration examples in which the hand illuminating section 16 is provided on a part other than the insertion portion 1*a* of the stereoscopic endoscope 1.

Note that the configurations of the hand illuminating section 16 and the hand illuminating switch 17 as shown in FIGS. 24 to 28 are not limited to being applied only to the stereoscopic endoscope 1 but can be widely applied to other endoscopes including a 2D endoscope.

Next, FIG. 29 is a diagram showing a configuration example in which the hand illuminating section 86 is provided on the hand side of the treatment instrument 8. The treatment instrument 8 is provided with the treatment portion 8*a* on a distal end side, the insertion portion 8*b* extended from the treatment portion 8*a* to the hand side, and an operation portion 8*c* connectedly arranged on a hand side of the insertion portion 8*b*. The operation portion 8*c* is provided with the hand illuminating section 86 and a hand illuminating switch 87.

By the way, in a case of switching between 3D observation by stereoscopy and normal 2D observation, there have been conventionally means such as operating an operation button for switching which is provided on the 3D monitor 5, and assigning functions to switches of an endoscope body to switch the observations by the switch of the endoscope body. However, since a switched state is reflected on all observers, it is not possible for each of the observers to perform 3D observation or 2D observation individually.

Especially, it is preferred for a surgeon and assistants to perform work such as a surgical operation while observing a 3D image having a deep stereoscopic effect. In a case of a circulating nurse or the like who frequently moves in an operating room, however, he not only observes the 3D monitor 5 but also performs various works such as preparing treatment instruments, gauze and the like while seeing his hands, and, therefore, there is a possibility that eye fatigue or visually induced motion sickness is caused by observing the 3D monitor 5 outside the visual field Q in stereoscopic observation or by frequently switching between observation of the 3D monitor 5 and observation of the actual field of view nearby.

Under such circumstances, it is preferred that each observer can choose between 2D observation and 3D observation as desired. Therefore, a configuration example in which such desired choice is enabled in a case where the 3D monitor 5 is of a polarization type and the pair of 3D observation glasses 7 is a pair of polarizing glasses will be described with reference to FIGS. 30 and 31.

Figure 30:
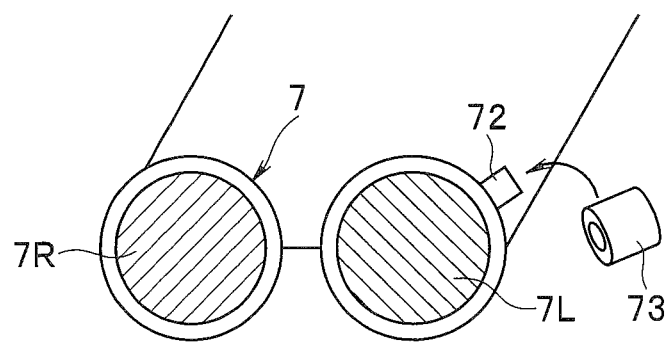
FIG. 30 is a diagram showing a configuration in which a knob cap is attached to a pair of 3D observation glasses which is capable of choosing between 2D observation and 3D observation in the above first embodiment.
Figure 31:
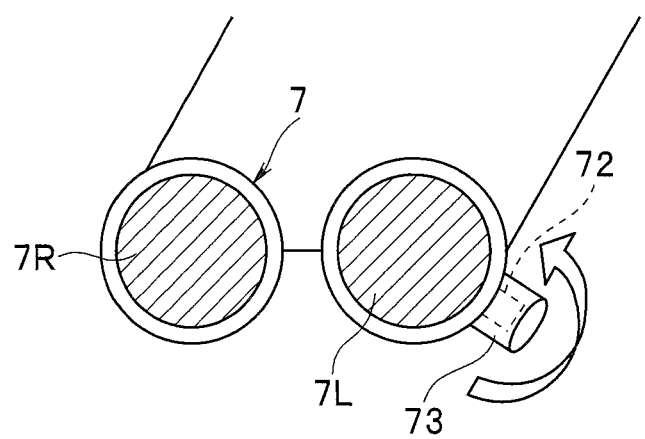
FIG. 31 is a diagram showing that the knob cap of the pair of 3D observation glasses is operated to switch between the 2D observation and the 3D observation in the above first embodiment.
Figure 32:
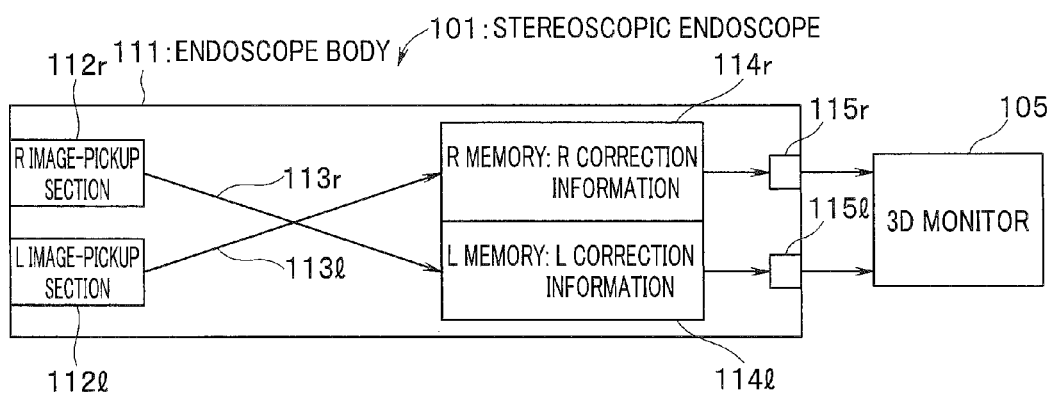
FIG. 32 is a block diagram showing a conventional configuration in which a stereoscopic endoscope in which right and left image pickup sections and right and left memories are reversely connected is observed on a 3D monitor.
Figure 33:
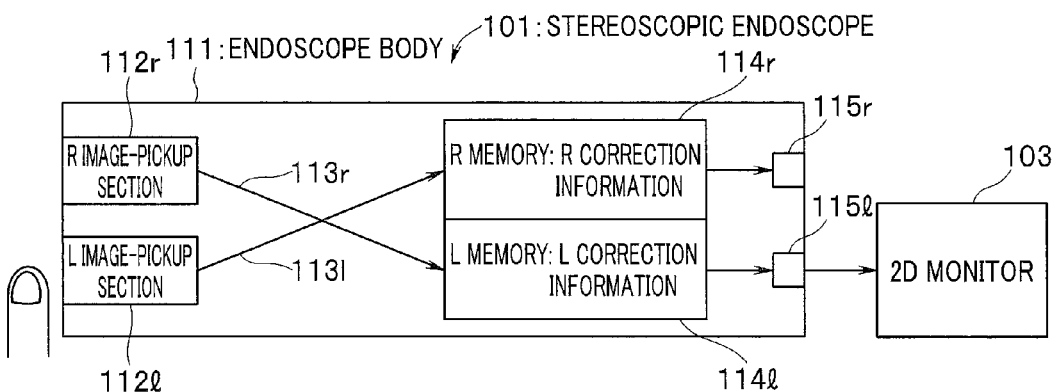
FIG. 33 is a block diagram showing a conventional configuration in which a manufacturing inspection of the stereoscopic endoscope shown in FIG. 32 is performed with use of a 2D monitor.
Figure 34:
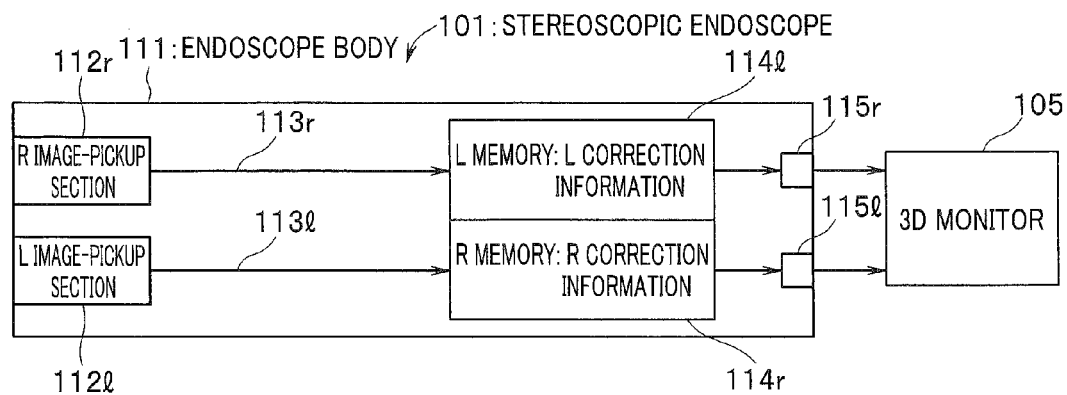
FIG. 34 is a block diagram showing a conventional configuration in which a stereoscopic endoscope in which pieces of correction information to be stored into memories are stored with left and right reversed is observed on a 3D monitor.
Figure 35:
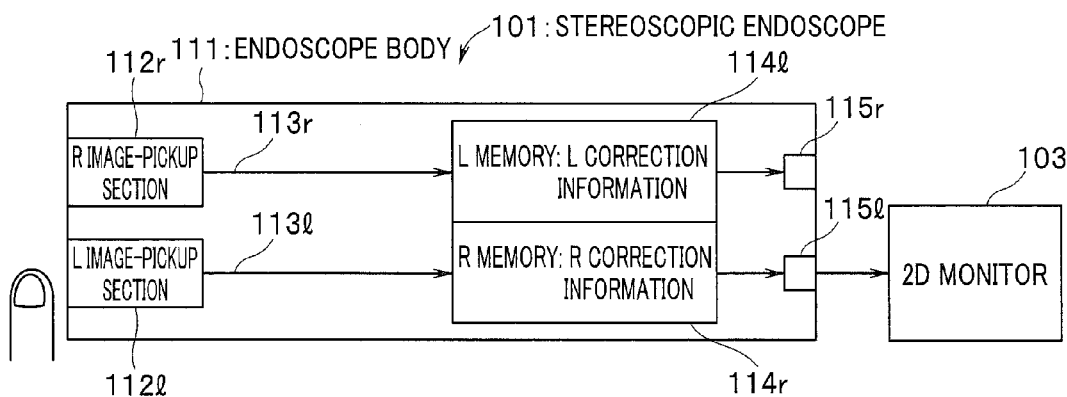
FIG. 35 is a block diagram showing a conventional configuration in which a manufacturing inspection of the stereoscopic endoscope shown in FIG. 34 is performed with use of a 2D monitor.

FIG. 30 is a diagram showing a configuration in which a knob cap is attached to a pair of 3D observation glasses which is capable of choosing between 2D observation and 3D observation; and FIG. 31 is a diagram showing that the knob cap of the pair of 3D observation glasses is operated to switch between the 2D observation and the 3D observation.

In the pair of 3D observation glasses 7 configured as a pair of polarizing glasses, polarization directions of a right eye polarizing filter 7R and a left eye polarizing filter 7L fitted to lens portions are different by 90° during stereoscopic observation.

Therefore, at least one of the right eye polarizing filter 7R and the left eye polarizing filter 7L is provided with a rotation mechanism capable of rotating a filter polarization direction around an observing line of sight by at least 90°, and a knob 72 for manually performing a rotation operation of the rotation mechanism.

Moreover, a sterilized knob cap 73 is detachably fitted to the knob 72. Thereby, even if an observer performs an operation of switching between 2D observation and 3D observation via the knob cap 73, a sterilized state of the observer is not damaged.

Note that it is possible to observe only a right eye image with both eyes by a rotation operation when the rotation mechanism is attached only to the left eye polarizing filter 7L side, and it is possible to observe only a left eye image with both eyes by a rotation operation when the rotation mechanism is attached only to the right eye polarizing filter 7R side.

Further, when the rotation mechanism is attached to both on the left eye polarizing filter 7L side and on the right eye polarizing filter 7R side, it is possible to observe any of a right eye image and a left eye image with both eyes as desired. However, when both of the rotation mechanisms are simultaneously operated, the right eye image is observed with a left eye, and the left eye image is observed with a right eye (reversed images are caused). Therefore, it is preferred to further provide a mechanism for, when a rotation operation of one of the polarizing filter is performed, inhibiting a rotation operation of the other polarizing filter (a mechanism for inhibiting simultaneous operations).

Further, rotation of the right eye polarizing filter 7R or the left eye polarizing filter 7L is not limited to being manually performed via the knob 72. The rotation may be electrically performed with use of a drive system such as a motor. In this case, a configuration is made in which an operation switch is provided on the pair of 3D observation glasses 7, and an operation of the drive system is performed according to an input operation from the operation switch. In this case, it is preferred to further fit the sterilized the knob cap 73 or the like to the operation switch, as described above.

Note that, even if the 3D monitor 5 is of the active shutter type or of a liquid crystal shutter type, it is possible for each observer to switch between 2D observation and 3D observation by himself by adopting the configuration of switching between 2D observation and 3D observation by a switch operation as described above.

Thus, according to the configuration shown in FIGS. 30 and 31, it is possible for each observer to switch between 2D observation and 3D observation as desired without discontinuing a surgical procedure, and, therefore, it becomes possible for each observer to choose an optimum 2D/3D observation mode according to a position relative to the 3D monitor 5 or as necessary.

Further, in the case of electrically switching between 2D observation and 3D observation using the drive system, the switching operation becomes smooth, and the switching operation can be performed by one press of the switch and the like. Therefore, the switching operation becomes easier than the case of rotating the knob 72 by 90 degrees, and it becomes possible to further shorten a time period during which a surgical operation is discontinued.

According to the first embodiment as above, pieces of correction information and pieces of identification information indicating right and left of the pieces of correction information are stored in right and left memories, respectively, and the pieces of identification information are image-combined with images outputted from right and left output sections, respectively. Therefore, by inserting, for example, a finger on a front of a right or left image pickup section, whether a right image or a left image can be confirmed. Moreover, by seeing the identification information combined with the image, it becomes possible to confirm whether correction information is for right or left. Thus, it is possible to prevent a reversed image, which is a left eye image observed by a right eye, or a reversed image, which is a right eye image observed by a left eye, and it is possible to prevent reversed correction, which is to correct a left eye image with right correction information, or reversed correction, which is to correct a right eye image with left correction information.

Further, by using the 2D monitor 3, it becomes possible to individually confirm an image with which identification information is combined, for each of the R and L output sections 15r and 15l. Further, in the case of using the 2D monitor 3 to which inputs of two systems can be inputted, it becomes possible to perform confirmations of right and left simultaneously.

By using a stereoscopic endoscope manufactured correctly through such a manufacturing inspection, it becomes possible to observe a correct stereoscopic image having no reversed right/left mistake or no right/left correction mistake by the 3D monitor 5.

A position of an observer relative to the 3D monitor 5 is detected; an observation center position is further acquired; and image shift of a 3D right eye image and a 3D left eye image is performed based on the observation center position. Therefore, it becomes possible to automatically and appropriately adjust a convergence angle when the 3D monitor 5 is seen from the observation center position. Therefore, it becomes possible for more observers to perform stereoscopic observation with an appropriate feeling of depth.

Further, since a position of a screen of the 3D monitor 5 is changed based on the observation center position, it is possible to automatically perform adjustment for causing the observation center position to be close to a center of a visual field Ω and makes it possible for more observers to perform appropriate stereoscopic observation.

In the case of providing the signal transmitting section 71 on the pair of 3D observation glasses 7 to detect a position of an observer based on a signal from the signal transmitting section 71, more reliable position detection becomes possible.

In the case of a plurality of observers, it is possible to obtain an appropriate observation center position without causing calculation to be excessively complicated by causing a mean value of positions of the plurality of observers to be the observation center position.

In addition, in the case of causing the signal transmitting section 71 of the pair of 3D observation glasses 7 to transmit a signal capable of identifying an individual, it is possible to obtain an observation center position by heavily weighting a particular observer. Thereby, it becomes possible to enable a main observer (for example, a chief surgeon) to be able to always perform observation at an optimum position.

Thus, according to the stereoscopic endoscope system of the present embodiment, it becomes possible to easily confirm whether there is a right/left mistake in manufacture of the stereoscopic endoscope 1.

Note that, though a stereoscopic endoscope system has been mainly described above, an operation method for causing the stereoscopic endoscope system to operate as described above is also possible. A processing program for causing a computer to operate the stereoscopic endoscope system as described above, a non-temporary computer-readable recording medium in which the processing program is recorded, and the like are also possible.

Further, the present invention is not limited to the above embodiments as they are, and the components can be modified and embodied within a range not departing from the spirit of the invention at a stage of practicing the invention. Further, various aspects of the invention can be formed by appropriately combining a plurality of components disclosed in the above embodiments. For example, some components may be deleted from all the components shown in the embodiments. Furthermore, components from different embodiments may be appropriately combined. Thus, it is, of course, possible to make various modifications and applications within the range not departing from the spirit of the invention.

What is claimed is:

1. A stereoscopic endoscope system comprising:
   a stereoscopic endoscope comprising:
      a right image pickup sensor configured to acquire a right eye image for generating a stereoscopic image;
      a left image pickup sensor configured to acquire a left eye image for generating the stereoscopic image;
      a right memory configured to store:
         right eye image correction information for correcting the right eye image; and
         right identification information identifying that what is stored by the right memory is the right eye image correction information;
      a left memory configured to store:
         left eye image correction information for correcting the left eye image; and
         left identification information identifying that what is stored by the left memory is the left eye image correction information;
      a right output interface circuit configured to output a right output comprising one of:
         a first identification information/image set comprising:
            the right eye image; and
            one of:
               a first set comprising:
                  the right eye image correction information; and
                  the right identification information; and
               a second set comprising:
                  the left eye image correction information; and
                  the left identification information; and
         a second identification information/image set comprising:
            the left eye image; and
            the other of:
               the first set; and
               the second set
      a left output interface circuit configured to output a left output comprising the other of:
         the first identification information/image set; and
         the second identification information/image set; and
      an identification information combining circuit configured to process at least one of:
         the right output to generate one of:
            a first combined image comprising the right image and the right identification information, based on the first identification information/image set;
            a second combined image comprising the right image and the left identification information, based on the first identification information/image set;
            a third combined image comprising the left image and the right identification information, based on the second identification information/image set; and
            a fourth combined image comprising the left image and the left identification information, based on the second identification information/image set; and
         the left output to generate one of:
            a fifth combined image comprising the left image and the left identification information, based on the second identification information/image set;
            a sixth combined image comprising the left image and the right identification information, based on the second identification information/image set;
            a seventh combined image comprising the right image and the right identification information, based on the first identification information/image set; and
            a eighth combined image comprising the right image and the left identification information, based on the first identification information/image set.

2. The stereoscopic endoscope system according to claim 1, further comprising a monitor configured to receive and display at least one of the first to eighth combined image.

3. The stereoscopic endoscope system according to claim 1,
   further comprising:
      a processor comprising hardware,
         wherein the processor is connectable to the right output interface circuit and the left output interface circuit, and
         wherein the processor is configured to generate a right eye image by correcting the right eye image with the right eye image correction information and a left eye image by correcting the left eye image with the left eye image correction information; and
      a three-dimensional (3D) monitor configured to display a stereoscopic image based on the right eye image and the left eye image corrected by the processor.

4. The stereoscopic endoscope system according to claim 3, further comprising an observation position detector configured to detect a position of each of one or more observers relative to the 3D monitor and acquire an observation center position based on the position of the each of the one or more observers detected,
   wherein the processor is configured to perform image shift of the right eye image and the left eye image so that a convergence angle is appropriate when the 3D monitor is seen from the observation center position.

5. The stereoscopic endoscope system according to claim 4,
wherein the monitor comprises:
a screen;
a display position adjusting mechanism configured to change a position of a screen of the screen; and
a display position controller configured to control the display position adjusting mechanism to change the position of the screen so that the observation center position comes closer to a center of a visual field, which is a range appropriate for stereoscopy of the 3D monitor.

6. The stereoscopic endoscope system according to claim 5, further comprising one or more pairs of 3D observation glasses, wherein each of the one or more pairs of 3D observation glasses are configured to enable stereoscopic observation according to a display system of the 3D monitor when an observer of the one or more observers wears the pair of 3D glasses, wherein
each of the one or more pairs of 3D observation glasses comprises a signal transmitter configured to transmit a signal receivable by the observation position detector, and
wherein the observation position detector is configured to detect the position of the observer wearing the pair of 3D observation glasses based on the signal received from the signal transmitter.

7. The stereoscopic endoscope system according to claim 6,
wherein in a case of one observer using the stereoscopic endoscope system, the observation position detector is configured to cause the position of the one observer to be the observation center position, and,
wherein in a case of a plurality of observers using the stereoscopic endoscope system, the observation position detector is configured to cause a mean value of the positions of the plurality of observers to be the observation center position.

8. The stereoscopic endoscope system according to claim 7, wherein
the signal the signal transmitted by the signal transmitter of the each of the one or more pairs of 3D observation glasses identifies an individuality of the respective pair of 3D observation glasses, and
wherein in the case of the plurality of observers, the observation position detector is configured to weight the positions of the plurality of observers according to which pairs of 3D observation glasses signals are received and calculate a mean value of the weighted positions of the observers, and then cause the mean value to be the observation center position, wherein the positions of the observers are detected based on the signals.

* * * * *

UNITED STATES PATENT AND TRADEMARK OFFICE
CERTIFICATE OF CORRECTION

| | | |
|---|---|---|
| PATENT NO. | : 9,848,758 B2 | Page 1 of 1 |
| APPLICATION NO. | : 14/967776 | |
| DATED | : December 26, 2017 | |
| INVENTOR(S) | : Ushijima | |

It is certified that error appears in the above-identified patent and that said Letters Patent is hereby corrected as shown below:

In the Claims

Column 25, Claim 5, Line 8 should read:
change a position of the screen; and

Column 25, Claim 6, Line 21 should read:
pair of 3D observation glasses, wherein Column 26, Claim 8, Line 14 should read:
the signal transmitted by the signal transmitter Signed and Sealed this
Fifth Day of June, 2018

Andrei Iancu
*Director of the United States Patent and Trademark Office*